United States Patent
Shusta et al.

(10) Patent No.: US 12,161,889 B2
(45) Date of Patent: Dec. 10, 2024

(54) BLOOD BRAIN BARRIER (BBB)-SELECTIVE ANTIBODIES AND METHODS OF USE THEREOF TO TARGET AGENTS TO THE BBB

(71) Applicant: Wisconsin Alumni Research Foundation, Madison, WI (US)

(72) Inventors: Eric V. Shusta, Madison, WI (US); Charles C. Stutz, Waltham, MA (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 957 days.

(21) Appl. No.: 17/260,697

(22) PCT Filed: Jul. 24, 2019

(86) PCT No.: PCT/US2019/043209
§ 371 (c)(1),
(2) Date: Jan. 15, 2021

(87) PCT Pub. No.: WO2020/023619
PCT Pub. Date: Jan. 30, 2020

(65) Prior Publication Data
US 2021/0277108 A1    Sep. 9, 2021

Related U.S. Application Data

(60) Provisional application No. 62/702,796, filed on Jul. 24, 2018.

(51) Int. Cl.
*C07K 16/28* (2006.01)
*A61P 25/00* (2006.01)

(52) U.S. Cl.
CPC .............. *C07K 16/28* (2013.01); *A61P 25/00* (2018.01); *C07K 2317/24* (2013.01); *C07K 2317/565* (2013.01); *C07K 2317/622* (2013.01)

(58) Field of Classification Search
CPC ................ C07K 16/28; C07K 2317/24; C07K 2317/565; C07K 2317/622; A61K 47/6803; A61P 25/00
See application file for complete search history.

(56) References Cited

U.S. PATENT DOCUMENTS

2015/0196663 A1    7/2015    Shusta

OTHER PUBLICATIONS

Abulrob A, et al. The blood-brain barrier transmigrating single domain antibody: mechanisms of transport and antigenic epitopes in human brain endothelial cells. Journal of Neurochemistry. 2005;95(4):1201-1214.

Altschul, S. F., et al. "Gapped BLAST and PSI-BLAST: a new generation of protein database search programs." Nucleic acids research 25.17 (1997): 3389-3402.
Boado RJ, et al. Humanization of anti-human insulin receptor antibody for drug targeting across the human blood-brain barrier. Biotechnology and Bioengineering. 2007;96(2):381-391.
Chen YH, et al. Molecular signatures of disease brain endothelia provide new sites for CNS-directed enzyme therapy. Nat Med. 2009; 15(10):1215-U1145.
Daneman R, et al. The mouse blood-brain barrier transcriptome: A new resource for understanding the development and function of brain endothelial cells. Plos One. 2010;5(10).
D'Angelo S, et al. The antibody mining toolbox: An open source tool for the rapid analysis of antibody repertoires. Mabs. 2014;6(1):160-172.
Enerson BE, et al. The rat blood-brain barrier transcriptome. Journal of Cerebral Blood Flow and Metabolism. 2006;26(7):959-973.
Farrington GK, et al. A novel platform for engineering blood-brain barrier-crossing bispecific biologics. FASEB Journal. 2014;28(11):4764-4778.
Georgiou G, et al. The promise and challenge of high-throughput sequencing of the antibody repertoire. Nature Biotechnology. 2014;32(2):158-168.
Goulatis Li, et al. Protein engineering approaches for regulating blood-brain barrier transcytosis. Current opinion in structural biology. 2017;45:109-115.
Helms HC, et al. In vitro models of the blood-brain barrier: An overview of commonly used brain endothelial cell culture models and guidelines for their use. Journal of Cerebral Blood Flow and Metabolism. 2016;36(5):862-890.
Hemadou A, et al. Pacific Biosciences Sequencing and IMGT/HighV-QUEST Analysis of Full-Length Single Chain Fragment Variable from an In Vivo Selected Phage-Display Combinatorial Library. Frontiers in immunology. 2017;8:1796.
Herrin, B. R., et al. "Structure and specificity of lamprey monoclonal antibodies." Proceedings of the National Academy of Sciences 105.6 (2008): 2040-2045.
Hu D, et al. Effective Optimization of Antibody Affinity by Phage Display Integrated with High-Throughput DNA Synthesis and Sequencing Technologies. PLoS One. 2015;10(6).
International Searching Authority. International Preliminary Report on Patentability for application PCT/ US2019/043209. Mailed on Jan. 26, 2021. 7 pages.
International Searching Authority. International Search Report and Written Opinion for application PCT/ US2019/043209. Mailed on Feb. 4, 2020. 17 pages.
Jones AR, et al. Blood-brain barrier transport of therapeutics via receptor-mediation. Pharmaceutical Research. 2007;24(9):1759-1771.
Jones AR, et al. Identifying blood-brain barrier selective single-chain antibody fragments. Biotechnology Journal. 2014;5:664-674.
Jones, P. T., et al. "Replacing the complementarity-determining regions in a human antibody with those from a mouse." Nature 321.6069 (1986): 522-525.
Karlin, S. et al. "Methods for assessing the statistical significance of molecular sequence features by using general scoring schemes." Proceedings of the National Academy of Sciences 87.6 (1990): 2264-2268.

(Continued)

*Primary Examiner* — Robert S Landsman
(74) *Attorney, Agent, or Firm* — Quarles & Brady, LLP

(57) ABSTRACT

The present invention provides antibodies or antigen binding fragments thereof including single chain variable fragment (scFv) antibodies that specifically bind to the blood brain barrier in vivo and methods of use.

21 Claims, 7 Drawing Sheets
Specification includes a Sequence Listing.

(56) References Cited

OTHER PUBLICATIONS

Kasahara, M. et al. "Two forms of adaptive immunity in vertebrates: similarities and differences." Advances in Immunology 122 (2014): 59-90.
Li, W., et al. "A quantitative MRI method for imaging blood-brain barrier leakage in experimental traumatic brain injury." PloS one 9.12 (2014): e114173.
Martin et al., Nanomaterials in Analytical Chemistry, Analytical Chemistry News &Features, May 1, 1998; pp. 322 A-327 A.
Muro S. Challenges in design and characterization of ligand-targeted drug delivery systems. Journal of Controlled Release. 2012; 164(2):125-137.
Muruganandam A, et al. Selection of phage-displayed llama single-domain antibodies that transmigrate across human blood-brain barrier endothelium. FASEB Journal. 2001;15(14):240.
Niedringhaus TP, et al. Landscape of next-generation sequencing technologies. Analytical Chemistry. 2011;83(12):4327-4341.
Nitta, T., et al. "Size-selective loosening of the blood-brain barrier in claudin-5-deficient mice." The Journal of cell biology 161.3 (2003): 653-660.
O'Connell D, et al. Phage versus phagemid libraries for generation of human monoclonal antibodies. Journal of Molecular Biology. 2002;321(1):49-56.
Pasqualini R, et al. Organ targeting in vivo using phage display peptide libraries. Nature. 1996;380(6572):364-366.
Poul MA, et al. Selection of tumor-specific internalizing human antibodies from phage libraries. Journal of Molecular Biology. 2000;301(5):1149-1161.
Presta, L. G. "Antibody engineering." Current Opinion in Structural Biology 2.4 (1992): 593-596.
Ravn U, et al. Deep sequencing of phage display libraries to support antibody discovery. Methods. 2013;60(1):99-110.
Riechmann, L, et al. "Reshaping human antibodies for therapy." Nature 332.6162 (1988): 323-327.
Roodink I, et al. Isolation of targeting nanobodies against co-opted tumor vasculature. Laboratory Investigation. 2010;90(1):61-67.
Safdari, Y., et al. "Antibody humanization methods—a review and update." Biotechnology and Genetic Engineering Reviews 29.2 (2013): 175-186.
Saito G, et al. Drug delivery strategy utilizing conjugation via reversible disulfide linkages: role and site of cellular reducing activities, Adv Drug Deliv Rev. Feb. 10, 2003; 55(2):199-215.
Sheets MD, et al. Efficient construction of a large nonimmune phage antibody library: The production of high-affinity human single-chain antibodies to protein antigens. Proceedings of the National Academy of Sciences of the United States of America. 1998;95(11):6157-6162.
Shi, Y., et al. "Rapid endothelial cytoskeletal reorganization enables early blood-brain barrier disruption and long-term schaemic reperfusion brain injury." Nature Communications 7 10523 (2016).
Stutz C, et al. Combinatorial approaches for the identification of bran drug delivery targets. Current Pharmaceutical Design. 2014;20(10):1564-1576.
Sugano et al., Antibody Targeting of Doxorubicin-loaded Liposomes Suppresses the Growth and Metastatic Spread of Established Human Lung Tumor Xenografts in Severe Combined Immunodeficient Mice Cancer Research 60, 6942-6949. 2000.
Sukhanova, A., et al. "Oriented conjugates of single-domain antibodies and quantum dots: toward a new generation of ultrasmall diagnostic nanoprobes." Nanomedicine: nanotechnology, biology and medicine 8.4 (2012): 516-525.
Thom, G., et al. (2018). Isolation of blood-brain barrier-crossing antibodies from a phage display library by competitive elution and their ability to penetrate the central nervous system. In MAbs (vol. 10, No. 2, pp. 304-314).
Trail P A, et al, Monoclonal antibody drug immunoconjugates for targeted treatment of cancer, Cancer Immunol Immunother. May 2003; 52(5):328-37.
Urich E, et al. Cargo Delivery into the Brain by in vivo identified Transport Peptides. Scientific Reports. 2015;5:14104.
Valadon P, et al. Screening phage display libraries for organ-specific vascular immunotargeting in vivo. Proceedings of the National Academy of Sciences of the United States of America. 2006; 103(2):407-412.
Van De Broek, B., et al. "Specific cell targeting with nanobody conjugated branched gold nanoparticles for photothermal therapy." ACS nano 5.6 (2011): 4319-4328.
Verma, R., et al. "Antibody engineering: comparison of bacterial, yeast, insect and mammalian expression systems." Journal of immunological methods 216.1-2 (1998): 165-181.
Wang XX, et al. Mining a yeast library for brain endothelial cell-binding antibodies. Nature Methods. 2007;4(2):143-145.
Wu A M, et al, Arming antibodies: prospects and challenges for immunoconjugates, Nat Biotechnol. Sep. 2005;23(9):1137-46.
Xu JL, et al. Diversity in the CDR3 region of V-H is sufficient for most antibody specificities. Immunity. 2000;13(1):37-45.
Yu YJ, et al. Boosting brain uptake of a therapeutic antibody by reducing its affinity for a transcytosis target. Science Translational Medicine. 2011;3(84).
Zhang X, et al. Creation and Evaluation of a Single-chain Antibody Tetramer that Targets Brain Endothelial Cells. AIChE Journal. 2014;60(4):1245-1252.
Zhou Y, et al. Identification of target and function specific antibodies for effective drug delivery. In: Dimitrov A, ed. Therapeutic Antibodies: Methods and Protocols. Totowa: Humana Press; 2009:145-160.
Zlokovic, et al. "Strategies to circumvent vascular barriers of the central nervous system." Neurosurgery 43.4(1998): 877-878.
Zuchero, Y.J.Y., et al. "Discovery of novel blood-brain barrier targets to enhance brain uptake of therapeutic antibodies." Neuron 89.1 (2016): 70-82.

BLOOD BRAIN BARRIER (BBB)-SELECTIVE ANTIBODIES AND METHODS OF USE THEREOF TO TARGET AGENTS TO THE BBB

CROSS-REFERENCE TO RELATED APPLICATIONS

This application is a national stage filing under 35 U.S.C. 371 of International Patent Application No. PCT/US2019/043209, filed Jul. 24, 2019, which claims priority to U.S. Provisional Application No. 62/702,796 filed on Jul. 24, 2018, the contents of both of which are incorporated by reference in their entirety.

STATEMENT REGARDING FEDERALLY SPONSORED RESEARCH

This invention was made with government support under NS071513 awarded by the National Institutes of Health and under HDTRA1-15-1-0012 awarded by the DOD/DTRA. The government has certain rights in the invention.

REFERENCE TO SEQUENCE LISTING SUBMITTED VIA EFS-WEB

This application is being filed electronically via EFS-Web and includes an electronically submitted Sequence Listing in .txt format. The .txt file contains a sequence listing entitled "2021_01_12_960296_04089_SEQ_LISTING" created on Jan. 12, 2021 and is 15,891 bytes in size. The Sequence Listing contained in this .txt file is part of the specification and is hereby incorporated by reference herein in its entirety.

BACKGROUND OF THE INVENTION

The field of the invention is related to blood brain barrier specific antibodies.

Although there has been substantial effort to identify novel blood-brain barrier (BBB) targeting molecules, only a handful of antibodies have been discovered that can successfully target the brain vasculature in vivo 1.2. Most of these antibodies were developed against specific BBB targets having elevated abundance at the BBB, such as the transferrin, insulin and basigin receptors 3-5. However, from gene and protein expression profiling alone, it is impossible to identify every potential protein that will allow targeting of the BBB since many proteins have unknown cellular localization and function 6.7. Thus, as a complement to profiling methods for target identification, combinatorial screens can be used to access these currently unknown targets. For instance, a combinatorial screen on an in vitro BBB model has yielded FC5, a camelid antibody that targets TMEM30A and can deliver pharmacologic amounts of therapeutic to brain tissue[8-10]. Unfortunately, while there are many in vitro cell-based BBB models that could be used as a screening substrate, there are no assurances that the identified antibodies and targets will have relevance in vivo since many key BBB properties are lost in culture[11]. For example, a combinatorial screen using an immortalized rat BBB cell line yielded 34 different antibodies that bound the in vitro BBB, but only one antibody was able to recognize an antigen at the BBB in vivo[12,13], and the most BBB selective antibody identified in another screen using primary cultured rat brain endothelial cells did not bind the in vivo BBB[14]. To enhance the in vivo relevance of combinatorial BBB screens, it is possible to perform in vivo screens centered on vascular administration of phage display libraries[15]. While several BBB binding peptides have been discovered by variations of in vivo phage display[1,16], peptides can be limited in their binding affinity and specificity. Despite the fact that antibodies may be preferable for some applications, and that several academic and industrial groups have attempted in vivo phage display screens with antibody libraries, there is only one example of successful in vivo phage antibody screening to identify an antibody that targets the glioblastoma vasculature[1,17].

One particular challenge that can confound brain-targeted in vivo phage display screens is that high amounts of background phage are recovered from the screening process. The problem of high background is exacerbated by the common practice for analyzing selection outputs that consists of post-screen random clone evaluation and assay of as many clones as possible (generally between 20 and 1,000). Thus, many interesting clones may be masked in a high background screen and therefore missed by random pool sampling, leading to a failed screen.

There is a need for antibodies that can target the blood brain barrier in vivo.

SUMMARY OF THE INVENTION

The present invention overcomes the aforementioned draw backs by providing antibodies developed through an in vivo screen and enriching BBB-targeting clones that may be masked by a large background signal. The present invention used next generation sequencing (NGS) to provide information regarding which antibody clones are in each pool, their abundance, and their round-to-round enrichment 18-20

In one aspect, the present disclosure provides an isolated blood brain barrier (BBB) antibody or antigen-binding fragment thereof comprising a heavy chain variable domain comprising a CDRH1 region of SEQ ID NO:2, a CDRH2 region of SEQ ID NO:3, and a CDRH3 region of SEQ ID NO:4 and a light chain variable domain comprising a CDRL1 region of SEQ ID NO:5, a CDRL2 region of SEQ ID NO:6, and a CDRL3 region of SEQ ID NO:7.

In another aspect, the present disclosure provides an isolated blood brain barrier (BBB) antibody or antigen-binding fragment thereof comprising a heavy chain variable domain comprising a CDRH1 region of SEQ ID NO:9, a CDRH2 region of SEQ ID NO:10, and a CDRH3 region of SEQ ID NO:11 and a light chain variable domain comprising a CDRL1 region of SEQ ID NO:12, a CDRL2 region of SEQ ID NO:13, and a CDRL3 region of SEQ ID NO: 14.

In another aspect, the present disclosure provides a BBB-selective antibody or antigen-binding fragment thereof wherein the antibody comprises SEQ ID NO:1 or SEQ ID NO:8.

In some aspects, the antibody is a single chain fragment variable (scFv).

In another aspect, the present disclosure provides a blood brain barrier (BBB)-selective antibody or antigen-binding fragment thereof comprising a peptide encoded by a DNA sequence comprising (a) SEQ ID NO:16, SEQ ID NO:17, SEQ ID NO:18, SEQ ID NO:19, SEQ ID NO:20 and SEQ ID NO:21, or (b) SEQ ID NO:23, SEQ ID NO:24, SEQ ID NO:25, SEQ ID NO:26, SEQ ID NO:27, and SEQ ID NO:28.

In another aspect, the present disclosure provides a blood brain barrier (BBB)-selective antibody or antigen-binding fragment thereof comprising a peptide encoded by a DNA sequence comprising SEQ ID NO:15 or SEQ ID NO:22.

In a further aspect, the present disclosure provides a vector comprising a DNA sequence that encodes the BBB-selective antibody described herein.

In yet another aspect, the present disclosure provides a method of targeting an agent to the blood brain barrier of a subject comprising the steps of (a) administering to the subject a BBB-selective antibody or antigen-binding fragment thereof as described herein, wherein the antibody is directly or indirectly linked to the agent.

The foregoing and other aspects and advantages of the invention will appear from the following description. In the description, reference is made to the accompanying drawings which form a part hereof, and in which there are shown, by way of illustration, preferred embodiments of the invention. Such embodiments do not necessarily represent the full scope of the invention, however, and reference is made therefore to the claims and herein for interpreting the scope of the invention.

DETAILED DESCRIPTION OF THE INVENTION

Before the present invention is described, it is understood that this invention is not limited to the particular methodology, protocols, and reagents described, as these may vary. It is also to be understood that the terminology used herein is for the purpose of describing particular embodiments only, and is not intended to limit the scope of the present invention which will be limited only by the appended claims.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference for the purpose of describing and disclosing the chemicals, cell lines, vectors, animals, instruments, statistical analysis and methodologies which are reported in the publications which might be used in connection with the invention. Nothing herein is to be construed as an admission that the invention is not entitled to antedate such disclosure by virtue of prior invention.

Figure 5:
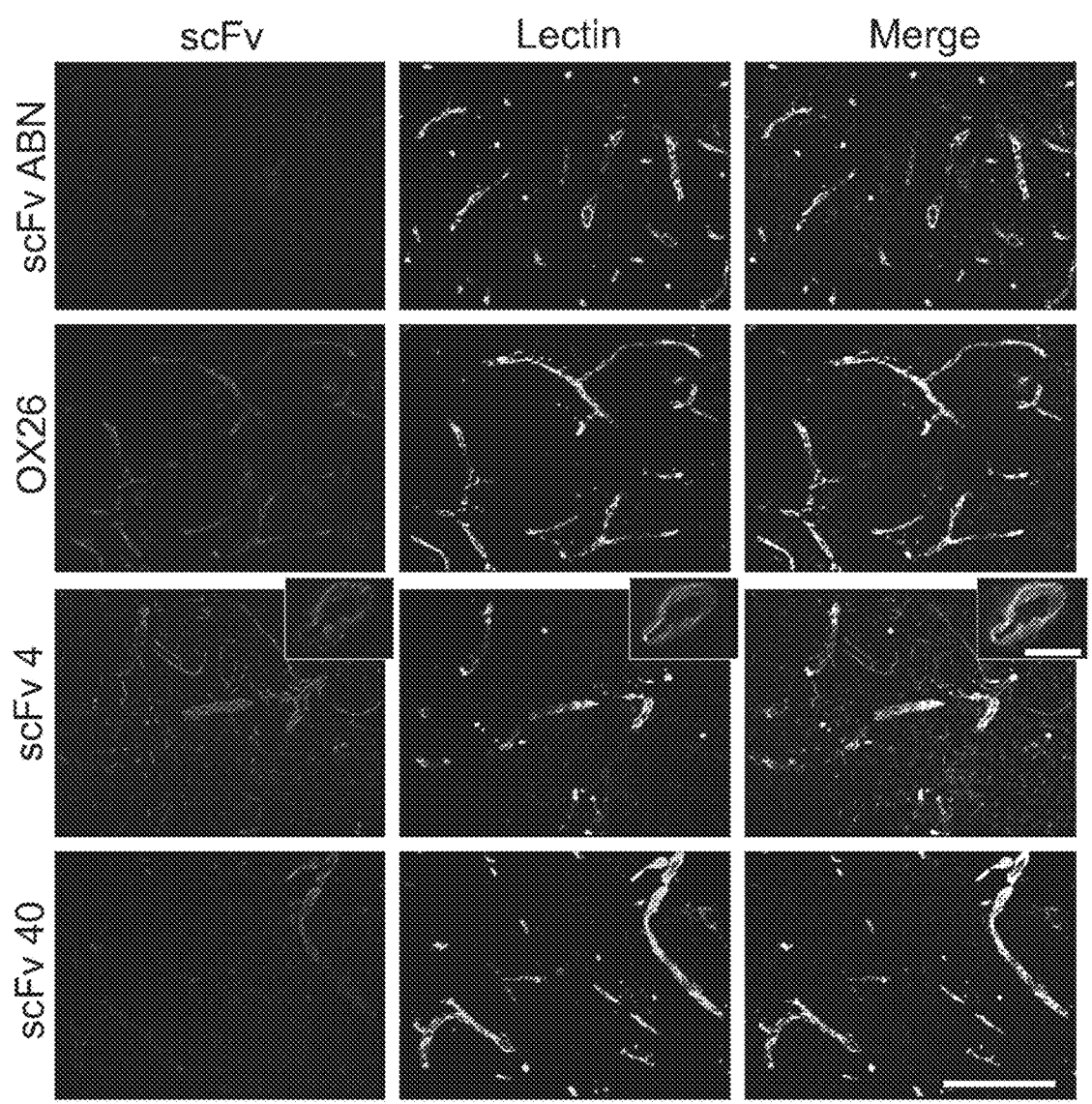
FIG. 5 are representative images of immunohistochemical analysis of selected scFv. Freshly frozen 7 μm rat brain tissue sections were immunolabeled with 50 μg/mL of scFv that had been pre-dimerized with anti c-myc antibody. Because scFv 40 could not be made in large quantities, a 4 μg/mL concentration was used. OX26 anti-transferrin receptor antibody was used as a positive binding control and ABN was used as a negative binding control. The sections were co-labeled with LEA-FITC to identify the brain microvessels. Enlarged inset is included to demonstrate that both the vascular wall and the cell processes are recognized by scFv40. The scale bar is 100 μm for each of the image panels, and the inset scale bar is 25 μm.
Figure 8:
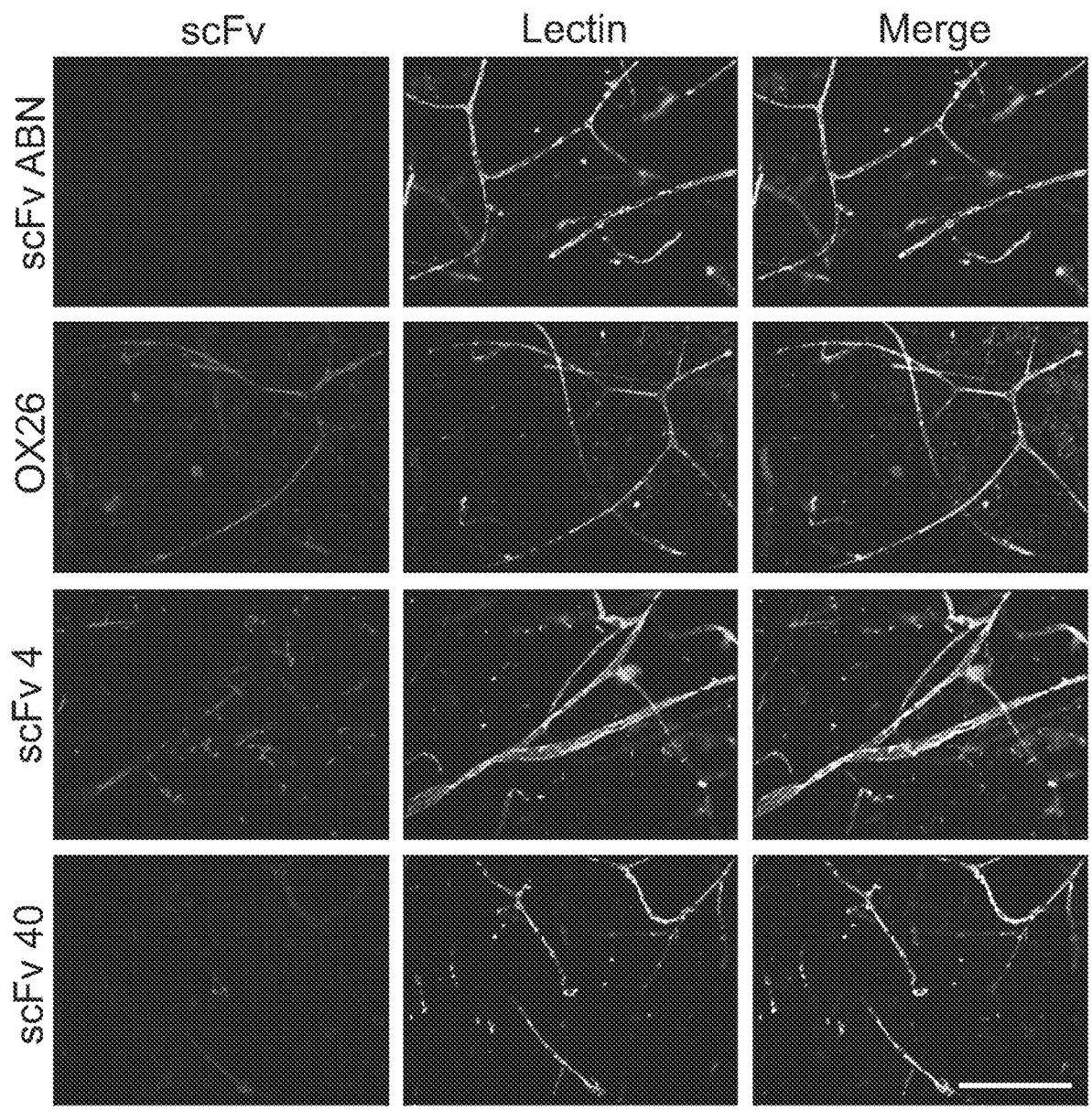
FIG. 8 are representative images of immunohistochemical analysis of selected scFv using vibratome brain tissue sections. Vibratome sections of freshly isolated rat brains were cut to 150 μm thickness. The sections were immunolabeled with 50 μg/mL of scFv that had been pre-dimerized with the anti-c-myc antibody. Because scFv 40 could not be made in large quantities, a 4 μg/mL concentration was used. OX26 anti-transferrin receptor antibody was used as a positive binding control and ABN was used as a negative binding control. The sections were co-labeled with LEA-FITC to identify the brain microvessels. The scale bar for the images is 100 μm.

The present invention provides antibodies that specifically/selectively bind to the blood brain barrier (BBB) in vivo. By using an in vivo screening method and next generation sequencing (NGS) analysis, two single chain variable fragments (scFvs), scFv4 (SEQ ID NO: 1) and scFv40 (SEQ ID NO:8) clearly bound antigens in rat brain in both frozen and fresh brain tissue sections (FIG. 5 and FIG. 8). ScFv 40 bound specifically to brain microvessels with continuous vessel labeling pattern similar to that of the anti-transferrin receptor antibody, OX26. However, unlike OX26 labeling which can be found throughout the brain, scFv 40 labeling was found only in small ventral brain regions, and infrequently appeared elsewhere throughout the brain cortex. In contrast to scFv 40, scFv 4 bound to both brain microvessels and to extended cellular processes that wrapped brain blood vessels, likely astrocytes (FIG. 5 and FIG. 8). Also, scFv4 binding could be observed throughout the brain. These two scFvs were not identified in the discrete sampling of 128 clones noted above, indicating the value of combining NGS with clonal evaluation.

The present disclosure provides in one embodiment an isolated antibody or antigen-binding fragment thereof capable of selectively binding to BBB. By "selectively" or "specifically" we mean an antibody capable of binding the surface of brain vessels but does not bind to lung, liver, or kidney tissue vasculature. By binding, we mean that the antibodies are capable of detection at a given tissue's endothelium by standard methods (e.g., tissue section immunofluorescence assays.) By "antibody" we mean to include single chain antibodies, such as scFv4 and scFv40, and antibody fragments, such as the polypeptides comprising CDR domains within scFv4 and scFv40, and chimeric antibodies containing the CDR domains within scFv4 and scFv40.

The terms "antibody" or "antibody molecule" are used herein interchangeably and refer to immunoglobulin molecules or other molecules which comprise an antigen binding domain. The term "antibody" or "antibody molecule" as used herein is thus intended to include whole antibodies (e.g., IgG. IgA. IgE, IgM, or IgD), monoclonal antibodies, polyclonal antibodies, chimeric antibodies, humanized antibodies, and antibody fragments, including single chain variable fragments (ScFv), single domain antibody, and antigen-binding fragments, genetically engineered antibodies, among others, as long as the characteristic properties (e.g., ability to bind BBB in vivo are retained).

As stated above, the term "antibody" includes "antibody fragments" or "antibody-derived fragments" which comprise an antigen binding domain. The term "antibody fragment" as used herein is intended to include any appropriate antibody fragment that displays antigen binding function, for example, Fab, Fab', F(ab')2, scFv. Fv, dsFv, ds-scFv, Fd, dAbs, TandAbs dimers, mini bodies, monobodies, diabodies, and multimers thereof and bispecific antibody fragments. Antibodies can be genetically engineered from the CDRs and ScFv4 and SV40 sequences described herein into antibodies and antibody fragments by using conventional techniques such as, for example, synthesis by recombinant techniques or chemical synthesis. Techniques for producing antibody fragments are well known and described in the art.

One may wish to engraft one or more CDRs from scFv4 or scFv40, the entire scFv, or fragments of the scFv into alternate scaffolds. For example, standard molecular biological techniques can be used to transfer the DNA sequences encoding the antibody's CDR(s) or scFv to (1) full IgG scaffold of human or other species: (2) another scFv scaffold of human or other species, or (3) other specialty vectors. If the CDR(s) have been transferred to a new scaffold all of the previous modifications described can also be performed. For example, one could consult *Biotechnol Genet Eng Rev.* 2013, 29:175-86 for a review of useful methods.

In one embodiment, an isolated blood brain barrier (BBB)-selective antibody or antigen-binding fragment thereof comprising a heavy chain variable domain comprising a CDRH1 region consisting of SEQ ID NO:2, a CDRH2 region consisting of SEQ ID NO:3, and a CDRH3 region consisting of SEQ ID NO:4 and a light chain variable domain comprising a CDRL1 region consisting of SEQ ID NO:5, a CDRL2 region consisting of SEQ ID NO:6, and a CDRL3 region consisting of SEQ ID NO:7. In another embodiment, an isolated blood brain barrier (BBB)-selective antibody or antigen-binding fragment thereof comprising a heavy chain variable domain comprising a CDRH1 region consisting of SEQ ID NO:9, a CDRH2 region consisting of SEQ ID NO:10, and a CDRH3 region consisting of SEQ ID NO:11 and a light chain variable domain comprising a CDRL1 region consisting of SEQ ID NO:12, a CDRL2 region consisting of SEQ ID NO: 13, and a CDRL3 region consisting of SEQ ID NO:14 is provided. In one embodiment, an isolated blood brain barrier (BBB)-selective antibody or antigen-binding fragment thereof comprising (a) a heavy chain variable domain comprising a CDRH1 region of SEQ ID NO:2, a CDRH2 region of SEQ ID NO:3, and a CDRH3 region of SEQ ID NO:4 and a light chain variable domain comprising a CDRL1 region of SEQ ID NO:5, a CDRL2 region of SEQ ID NO:6, and a CDRL3 region of SEQ ID NO:7, or (b) a heavy chain variable domain comprising a CDRH1 region of SEQ ID NO:9, a CDRH2 region of SEQ ID NO: 10, and a CDRH3 region of SEQ ID NO:11 and a light chain variable domain comprising a CDRL1 region of SEQ ID NO: 12, a CDRL2 region of SEQ ID NO: 13, and a CDRL3 region of SEQ ID NO: 14 is provided.

In some embodiments, the BBB-selective antibody or antigen-binding fragment is engrafted within a full IgG scaffold of human or other species or a scFv scaffold of human or other species.

In a further exemplary embodiment, the BBB-selective antibody or antigen-binding fragment thereof comprises, consists essentially of, consists of SEQ ID NO:1 (scFv4) or SEQ ID NO:8 (scFv40).

In some embodiments, for example, the invention may be an expression vector that includes a polynucleotide encoding scFv4 or scFv40 (e.g., SEQ ID NO:1 or 8, respectively). In some embodiments, the vector comprises the polynucleotide sequences set forth in SEQ ID NOs: 15 or 22 or other degenerate tricodons that yield the same amino acid sequence. In other embodiments, the invention may be an expression vector that encodes the isolated blood brain barrier (BBB)-selective antibody or antigen-binding fragment thereof comprising a heavy chain variable domain comprising a CDRH1 region consisting of SEQ ID NO:2, a CDRH2 region consisting of SEQ ID NO:3, and a CDRH3 region consisting of SEQ ID NO:4 and a light chain variable domain comprising a CDRL1 region consisting of SEQ ID NO:5, a CDRL2 region consisting of SEQ ID NO:6, and a CDRL3 region consisting of SEQ ID NO:7. In another embodiment, the expression vector encodes an isolated blood brain barrier (BBB)-selective antibody or antigen-binding fragment thereof comprising a heavy chain variable domain comprising a CDRH1 region consisting of SEQ ID NO:9, a CDRH2 region consisting of SEQ ID NO: 10, and a CDRH3 region consisting of SEQ ID NO:11 and a light chain variable domain comprising a CDRL1 region consisting of SEQ ID NO:12, a CDRL2 region consisting of SEQ ID NO:13, and a CDRL3 region consisting of SEQ ID NO:14.

In other embodiments, the nucleotide or protein sequence comprises conservative or inconsequential substitutions or deletions.

In other embodiments, the invention includes a purified and isolated host cell comprising an expression vector containing an isolated nucleic acid capable of encoding a BBB-selective antibody, for example, encoding the amino acid sequence set forth in SEQ ID NOs: 1 or 8. It should be appreciated that the host cell can be any cell capable of expressing antibodies, for example fungi: mammalian cells: insect cells, using, for example, a baculovirus expression system: plant cells, such as, for example, corn, rice, *Arabidopsis*, and the like. See, generally, Verma, R. et al., J Immunol Methods. 1998 Jul. 1: 216(1-2): 165-81.

The antibodies or antibody fragments can be wholly or partially synthetically produced. Thus the antibody may be from any appropriate source, for example recombinant sources and/or produced in transgenic animals or transgenic plants. Thus, the antibody molecules can be produced in vitro or in vivo. Preferably the antibody or antibody fragment comprises an at least the heavy chain variable region ($V_H$) which generally comprises the antigen binding site. In preferred embodiments, the antibody or antibody fragment comprises the heavy chain variable region and light chain variable region ($V_L$). The antibody or antibody fragment can be made that comprises all or a portion of a heavy chain constant region, such as an IgG1, IgG2, IgG3, IgG4, IgA1, IgA2, IgE, IgM or IgD constant region.

Furthermore, the antibody or antibody fragment can comprise all or a portion of a kappa light chain constant region or a lambda light chain constant region. All or part of such constant regions may be produced wholly or partially synthetic. Appropriate sequences for such constant regions are well known and documented in the art.

The term "fragment" as used herein refers to fragments of biological relevance (functional fragment), e.g., fragments which can contribute to or enable antigen binding, e.g., form part or all of the antigen binding site or can contribute to the prevention of the antigen interacting with its natural ligands. Fragments in some embodiments comprise a heavy chain variable region ($V_H$ domain) and light chain variable region ($V_L$) of the invention. In some embodiments, the fragments comprise one or more of the heavy chain complementarity determining regions (CDRHs) of the antibodies or of the $V_H$ domains, and one or more of the light chain complementarity determining regions (CDRLs), or $V_L$ domains to form the antigen binding site. For example, a fragment is suitable for use in the present methods and kits if it retains its ability to bind in vivo to the BBB.

The term "complementarity determining regions" or "CDRs," as used herein, refers to part of the variable chains in immunoglobulins (antibodies) and T cell receptors, generated by B-cells and T-cells respectively, where these molecules bind to their specific antigen. As the most variable parts of the molecules, CDRs are crucial to the diversity of antigen specificities generated by lymphocytes. There are three CDRs (CDR1, CDR2 and CDR3), arranged non-consecutively, on the amino acid sequence of a variable domain of an antigen receptor. Since the antigen receptors are typically composed of two variable domains (on two different polypeptide chains, heavy and light chain), there are six CDRs for each antigen receptor that can collectively come into contact with the antigen. A single whole antibody molecule has two antigen receptors and therefore contains twelve CDRs. Sixty CDRs can be found on a pentameric IgM molecule.

Within the variable domain, CDR1 and CDR2 may be found in the variable (V) region of a polypeptide chain, and CDR3 includes some of V, all of diversity (D, heavy chains only) and joining (J) regions. Since most sequence variation associated with immunoglobulins and T cell receptors is found in the CDRs, these regions are sometimes referred to as hypervariable regions. Among these, CDR3 shows the greatest variability as it is encoded by a recombination of VJ in the case of a light chain region and VDJ in the case of heavy chain regions. The tertiary structure of an antibody is important to analyze and design new antibodies.

The term "single-chain variable fragment," "single-chain fragment variable" or "scFv," as used herein, refers to a fusion protein of the variable regions of the heavy ($V_H$) and light chains ($V_L$) of immunoglobulins, connected with a short linker peptide of ten to about 25 amino acids. The linker may usually be rich in glycine for flexibility, as well as serine or threonine for solubility, and can either connect the N-terminus of the $V_H$ with the C-terminus of the $V_L$, or vice versa. scFvs may often be produced in microbial cell cultures such as *E. coli* or *Saccharomyces cerevisiae*.

ScFvs have many uses, e.g., flow cytometry, immunohistochemistry, and as antigen-binding domains of artificial T cell receptors. In one embodiment, the present invention discloses scFvs. In one embodiment, a scFvs can be designed and made that contain the three heavy chain variable domains, CDRH1, CDRH2, and CDRH3, e.g., SEQ ID NOs: 2, 3 and 4 or SEQ ID Nos: 9, 10 and 11, and three light chain variable domains, CDRL1. CDRL2 and CDRL3, e.g., SEQ ID NOs:5, 6 and 7 or SEQ ID NO: 12, 13 and 14 respectively.

In one embodiment, the antibody or fragment comprises CDRH1, CDRH2 and CDRH3 of (a) SEQ ID NO: 2, SEQ ID NO:3, and SEQ ID NO. 4 or (b) SEQ ID NO: 9, SEQ ID NO:10, and SEQ ID NO:11, respectively. In further embodiments, the antibody or fragment comprises CDRL1, CDRL2 and CDRL3 of (a) SEQ ID NO:5, SEQ ID NO:6, and SEQ ID NO:7, or (b) SEQ ID NO:12, SEQ ID NO: 13, and SEQ ID NO:14, respectively. In some embodiments, additional polypeptide sequence is found linking the CDR1, CDR2 and CDR3 in order to allow for the formation of the proper three dimensional antigen binding site of the antibody or fragment so that the antibody or fragment is capable of binding to BBB.

In another embodiment, the antibody comprises, consists essentially of, consists of or is the polypeptide of SEQ ID NO: 1 or SEQ ID NO:8.

In some embodiments, the antibodies have substantial identity to the polypeptide found in SEQ ID NO:1. In some embodiments, the antibodies have at least 50% identity to SEQ ID NO:1, alternatively at least 75% sequence identity, alternatively at least 80% sequence identity, alternatively at least 90% sequence identity, alternatively at least 95% sequence identity, alternatively at least 98% sequence identity, alternatively at least 100% sequence identity. In some embodiments, the modified protein has at least 100% sequence identity within CDRH1, CDRH2 and CDRH3 within SEQ ID NO:1 (e.g. SEQ ID Nos. 2-4). In some embodiments, the antibodies further have 100% sequence identity with CDRL1, CDRL2 and CDRL3 within SEQ ID NO:1 (e.g. SEQ ID NO:5, SEQ ID NO:6, and SEQ ID NO:7).

In some embodiments, the antibodies have substantial identity to the protein found in SEQ ID NO:8. In some embodiments, the antibodies have at least 50% identity to SEQ ID NO:8, alternatively at least 75% sequence identity, alternatively at least 80% sequence identity, alternatively at least 90% sequence identity, alternatively at least 95% sequence identity alternatively at least 98% sequence identity, alternatively at least 100% sequence identity. In some embodiments, the modified protein has at least 100% sequence identity within CDRH1, CDRH2 and CDRH3 within SEQ ID NO:8 (e.g. SEQ ID Nos. 9-11). In some embodiments, the antibodies further have 100% sequence identity with CDRL1, CDRL2 and CDRL3 within SEQ ID NO:8 (e.g. SEQ ID NO:12, SEQ ID NO: 13, and SEQ ID NO:14).

Protein and nucleic acid sequence identities are evaluated using the Basic Local Alignment Search Tool ("BLAST") which is well known in the art (Karlin and Altschul, 1990, *Proc. Natl. Acad. Sci. USA* 87: 2267-2268; Altschul et al., 1997, *Nucl. Acids Res.* 25: 3389-3402). The BLAST programs identify homologous sequences by identifying similar segments, which are referred to herein as "high-scoring segment pairs." between a query amino or nucleic acid sequence and a test sequence which is preferably obtained from a protein or nucleic acid sequence database. Preferably, the statistical significance of a high-scoring segment pair is evaluated using the statistical significance formula (Karlin and Altschul, 1990), the disclosure of which is incorporated by reference in its entirety. The BLAST programs can be used with the default parameters or with modified parameters provided by the user.

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" of polynucleotide sequences means that a polynucleotide comprises a sequence that has at least 25% sequence identity. Alternatively, percent identity can be any integer from 25% to 100%. More preferred embodiments include at least: 25%, 30%, 35%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98% or 99% compared to a reference sequence using the programs described herein: preferably BLAST using standard parameters, as described. These values can be appropriately adjusted to determine corresponding identity of proteins encoded by two nucleotide sequences by taking into account codon degeneracy, amino acid similarity, reading frame positioning and the like.

"Substantial identity" of amino acid sequences for purposes of this invention normally means polypeptide sequence identity of at least 40%. Preferred percent identity of polypeptides can be any integer from 40% to 100%. More preferred embodiments include at least 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, %, or 99%.

The terms "monoclonal antibody" or "monoclonal antibody composition" as used herein refer to a preparation of antibody molecules of a single amino acid composition. The monoclonal antibody also includes "human monoclonal antibody" which refers to antibodies displaying a single binding specificity which have variable and constant regions derived from human germline immunoglobulin sequences. The human monoclonal antibodies can be produced by a hybridoma which includes a B cell obtained from a transgenic nonhuman animal, for example, a transgenic mouse, having a genome comprising a human heavy chain transgene and a light human chain transgene fused to an immortalized cell.

The term "chimeric antibody" refers to an antibody comprising a variable region, i.e., binding region, from one source or species and at least a portion of a constant region derived from a different source or species, usually prepared by recombinant DNA techniques. Other forms of "chimeric antibodies" are those in which the class or subclass has been modified or changed from that of the original antibody. Such "chimeric" antibodies are also referred to as "class-switched antibodies." Methods for producing chimeric antibodies involve conventional recombinant DNA and gene transfection techniques now well known in the art.

The term "antibody" also shall include humanized antibody, human antibody and recombinant human antibody. The term "humanized antibody" refers to antibodies in which the human framework have been modified to comprise fragments of antibodies taken from a different species that provide specificity to an antigen and includes "humanized" forms of non-human (e.g., murine, rat, etc.) antibodies (including antigen-binding fragments thereof), which are chimeric antibodies containing minimal sequence derived from non-human immunoglobulin. Humanized antibodies include human immunoglobulins or fragments thereof in which hypervariable region residues of the human antibody or fragment are replaced by hypervariable region residues from a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. In some instances, humanized antibodies may comprise residues which are not found in the recipient antibody or in the donor antibody and are made to further refine antibody performance. In general, the humanized antibody will comprise substantially all of at least one, and typically two or three variable domains, in which all or substantially all of the hypervariable loops correspond to those of a non-human immunoglobulin and all or substantially all of the FR regions are those of a human immunoglobulin sequence. In some aspects, the humanized antibody optionally also will comprise at least a portion of an immunoglobulin constant region (Fc), typically that of a human immunoglobulin. For further details, see Jones et al., Nature 321:522-525 (1986): Reichmann et al., Nature 332:323-329 (1988); and Presta, *Curr. Op. Struct. Biol.* 2:593-596 (1992). For example, in one embodiment, the invention provides a humanized scFv antibody or antigen binding fragment thereof comprising the CDR domains from scFV4 or scFV40) described herein.

The antibodies disclosed in the present invention may be modified to be human antibodies which include the constant region from a human germline immunoglobulin sequences. The term "recombinant human antibody" or "chimeric human antibody" includes all human antibodies that are prepared, expressed, created or isolated by recombinant means, such as antibodies isolated from a host cell such as an SP2-0, NS0 or CHO cell (like CHO K1) or from an animal (e.g., a mouse) that is transgenic for human immunoglobulin genes or antibodies or polypeptides expressed using a recombinant expression vector transfected into a host cell. Such recombinant human antibodies have variable and in some embodiments, constant regions derived from human germline immunoglobulin sequences in a rearranged form.

As used herein, the terms "proteins" and "polypeptides" are used interchangeably herein to designate a series of amino acid residues connected to the other by peptide bonds between the alpha-amino and carboxy groups of adjacent residues. The terms "protein" and "polypeptide" refer to a polymer of protein amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to an encoded gene product and fragments thereof. Thus, exemplary polypeptides or proteins include gene products, naturally occurring proteins, homologs, orthologs, paralogs, fragments and other equivalents, variants, fragments, and analogs of the foregoing. The antibodies of the present invention are polypeptides.

In one embodiment, the antibody is selected from the group consisting of a single chain variable fragment (scFv) antibody, an antigen-binding fragment and a chimeric antibody, for example, a humanized antibody (chimeric human antibody).

In some embodiments, the isolated antibody or fragment thereof is directly or indirectly linked to an agent. In some embodiments, the antibody or fragment thereof is conjugated to the agent. In other embodiments, the agent is a polypeptide, wherein the polypeptide is translated concurrently with the antibody polypeptide sequence.

The term "agent" as used herein includes any useful moiety that allows for the purification, identification, detection, diagnosing, imaging, or therapeutic use of the antibody of the present invention. The terms agent includes epitope tags, detection markers and/or imaging moieties, including, for example, enzymatic markers, fluorescence markers, radioactive markers, among others. Additionally, the term agent includes therapeutic agents, pharmaceutical agents and compounds, small molecules, and drugs, among others. The term agent also includes diagnostic agents. The agent to be attached to an antibody described herein is selected according to the purpose of the intended application (i.e, treatment of a particular disease). Such agents may include but is not limited to, for example, pharmaceutical agents, biologics, toxins, fragments of toxins, alkylating agents, enzymes, antibiotics, antimetabolites, antiproliferative agents, hormones, neurotransmitters, DNA. RNA, siRNA, oligonucleotides, antisense RNA, aptamers, diagnostics, radioopaque dyes, radioactive isotopes, fluorogenic compounds, magnetic labels, nanoparticles, marker compounds, lectins, compounds which alter cell membrane permeability, photochemical compounds, small molecules, liposomes, micelles, gene therapy vectors, viral vectors, and the like. In some embodiments, the antibody is linked to a biologic that can be targeted to the brain or BBB. For example, in one embodiment, the biologics include, but are not limited to, for example, proteinaceous components, for example, other antibody binding domains, trophic factors, neuroactive peptides, among others.

For use herein, the term "antibody conjugate" includes an antibody described above linked directly or indirectly to an agent.

Suitable epitope tags are known in the art and include, but are not limited to, 6-Histidine (His), hemagglutinin (HA), cMyc, GST, Flag (DYKDDDDK) tag, V5 tag, NE-tag, among others. Epitope tags are commonly used as a purification tag. A purification tag is an agent that allows isolation of the antibody from other non-specific proteins.

In one embodiment of the invention, the antibody of the invention is linked with an agent, for example, with a detectable marker, preferably a fluorescent, enzymatic or a luminescent marker. Examples of suitable enzymes include, but are not limited to, horseradish peroxidase, alkaline phosphatase, beta-galactosidase, glucose-6-phosphatase, or acetylcholinesterase. Examples of suitable tags comprising prosthetic group complexes include, but are not limited to, streptavidin/biotin and avidin/biotin. Examples of suitable fluorescent materials include, but are not limited to, fluorescein, fluorescein isothiocyanate, rhodamine, dichlorot[pi]azinylamine fluorescein, green fluorescent protein (GFP), red fluorescent protein (RFP), blue fluorescent dyes excited at wavelengths in the ultraviolet (UV) part of the spectrum (e.g. AMCA (7-amino-4-methylcoumarin-3-acetic acid): Alexa Fluor 350), green fluorescent dyes excited by blue light (e.g. FITC, Cy2, Alexa Fluor 488), red fluorescent dyes excited by green light (e.g. rhodamines, Texas Red, Cy3, Alexa Fluor dyes 546, 564 and 594), or dyes excited with infrared light (e.g. Cy5) to be visualized with electronic detectors (CCD cameras, photomultipliers): dansyl chloride, phycoerythrin or the like.

Suitable examples of radioactive material include, but are not limited to, $^{125}$I, $^{131}$I, $^{35}$S or $^{3}$H. In some embodiments, the antibody is directly or indirectly linked to a radioisotope, an NMR or MRI contrast agent or nanoparticles for diagnosing, imaging and treatment.

Suitable nanoparticles, including metal nanoparticles and other metal chelates, are known in the art and include, but are not limited to, for example, gold nanoparticles (B. Van de Broek et al., ACSNano, Vol. 5, No. 6, 4319-4328, 2011), quantum dots (A. Sukhanova et al., Nanomedicine, 8 (2012) 516-525), magnetic nanoparticles ($Fe_3O_4$), silver nanoparticles, nanoshells and nanocages.

As used herein, the phrase "antibody in combination with a pharmaceutically active compound" shall not be limited by the method of manufacture and such compositions may be produced by, but not limited to, techniques of conjugating, linking, coupling and decorating known in the art.

In general, methods of conjugating, linking and coupling antibodies to pharmacologically active compounds are well known in the field. For example, see, Wu A M, Senter P D, Arming antibodies: prospects and challenges for immunoconjugates, Nat Biotechnol. 2005 September: 23(9): 1137-46 and Trail P A, King H D, Dubowchik G M, Monoclonal antibody drug immunoconjugates for targeted treatment of cancer, Cancer Immunol Immunother. 2003 May: 52(5): 328-37; Saito G, Swanson J A, Lee K D. Drug delivery strategy utilizing conjugation via reversible disulfide linkages: role and site of cellular reducing activities, Adv Drug Deliv Rev. 2003 Feb. 10: 55(2): 199-215.

The BBB-targeting antibodies may be provided in combination with liposome, nanoparticles or other analogous carriers loaded with a pharmaceutically active compound. Methods of preparing such compositions are known in the field (see, for example, Sugano et al., Antibody Targeting of Doxorubicin-loaded Liposomes Suppresses the Growth and Metastatic Spread of Established Human Lung Tumor Xenografts in Severe Combined Immunodeficient Mice Cancer Research 60, 6942-6949 Dec. 15, 2000 and Martin et al., Nanomaterials in Analytical Chemistry, Analytical Chemistry News &Features, May 1, 1998; pp. 322 A-327 A). As used herein, the phrase "antibody in combination with a pharmaceutically active compound" shall not be limited by the method of manufacture and such compositions may be produced by, but not limited to, techniques of conjugating, linking, coupling and decorating known in the art.

The following is a prophetic description of covalent chemical linkage of a proposed BBB-selective antibody to a pharmacologically active or therapeutic compound:

One may wish to link the antibodies of the present invention and active compounds via primary amines, for example as taken from Jones, A. R. and E. V. Shusta, Blood-brain barrier transport of therapeutics via receptor-mediation. Pharmaceutical Research, 2007. 24(9): p. 1759-1771. Lysine residues of either targeting vector (the scFv sequences) or protein therapeutic would be functionalized using Traut's reagent (2-iminothiolane.HCL) yielding a thiol. The thiol group, now attached to the lysine residue, is reacted with a maleimide-functionalized drug or vector resulting in a stable thio-ether bond. (One may or may not use a chemical spacer such as poly-ethylene glycol to reduce steric hindrance).

One may wish to use non-covalent linkage of the proposed antibody to pharmacologically active component. For example, one could use biotin/streptavidin interaction, such as the disclosure taken from Jones, A. R. and E. V. Shusta, Blood-brain barrier transport of therapeutics via receptor-mediation. Pharmaceutical Research, 2007. 24(9): p. 1759-1771.

Lysine residues of either the targeting vector or the protein therapeutic would be biotinylated using one of a number of commercial methods (such as N-hydroxysuccinimide biotin analogs). Then, either the vector or the therapeutic (whichever one was not modified in the previous step) would be conjugated to streptavidin or one of its variants (e.g., neutravidin) using one of the other methods presented here. The monobiotinylated reagent and the streptavidin conjugated counterpart would be combined and the near-covalent binding affinity would keep the reagents together.

One may wish to express the antibody as a fusion protein with a pharmacologically or therapeutically relevant peptide. For example, one may wish to express a scFv of the present invention with a protein linker and a protein therapeutic. Standard molecular biology techniques (e.g., restriction enzyme based subcloning, or homology based subcloning) could be used to place the DNA sequence encoding a protein therapeutic in frame with the targeting vector (usually a protein linker is also added to avoid steric hindrance). The fusion protein is then produced as one peptide in a host cell (e.g., yeast. bacteria, insect, or mammalian cell) and purified before use. Note the therapeutic does not need to be a whole protein. (For example, it can be a single peptide chain as a subunit in a protein with more than one peptide. The other peptides can be co-expressed with the vector fusion and allowed to associate in the host cell or after secretion).

In some embodiments of the present invention, antibodies or fragments may be administered with or without the above modifications. One may wish to administer the antibodies of the present invention without the modifications described above. For example, one may administer the antibodies through an intravenous injection or through intra-peritoneal and subcutaneous methods.

Further embodiments contemplated include antibody-drug conjugates. For example, suitable drugs may be conjugated to the antibodies or fragments described herein with a cleavable or non-cleavable linker. Cleavable and non-cleavable linkers are known in the art.

Conventional linking methods of linking a substance of interest to a polypeptide, in particular an antibody, are known in the art (e.g., See TERNYNCK and AVRAMEAS, 1987, "Techniques immunoenzymatiques" Ed. INSERM, Paris or G. T. Hermanson, Bioconjugate Techniques, 2010, Academic Press). Many chemical cross-linking methods are also known in the art. Cross-linking reagents may be homobifunctional (i.e., having two functional groups that undergo the same reaction) or heterobifunctional (i.e., having two different functional groups). Numerous cross-linking reagents are commercially available. Detailed instructions for their use are readily available from the commercial suppliers. A general reference on polypeptide cross-linking and conjugate preparation is: WONG, Chemistry of protein conjugation and cross-linking, CRC Press (1991).

In further embodiments, the agent is a therapeutic agent. As used herein, the term "therapeutic agent" refers to any synthetic or naturally occurring biologically active compound or composition of matter which, when administered to an organism (human or nonhuman animal), induces a desired pharmacologic, immunogenic, and/or physiologic effect by local and/or systemic action. The term therefore encompasses those compounds or chemicals traditionally regarded as drugs, chemotherapeutics, and biopharmaceuticals including molecules such as proteins, peptides, hormones, nucleic acids, gene constructs and the like. Examples of therapeutic agents are described in well-known literature references such as the Merck Index (14th edition), the Physicians' Desk Reference (64th edition), and The Pharmacological Basis of Therapeutics (12th edition), and they include, without limitation, substances used for the treatment, prevention, diagnosis, cure or mitigation of a disease or illness: substances that affect the structure or function of the body, or pro-drugs, which become biologically active or more active after they have been placed in a physiological environment.

Further embodiments provide an isolated nucleic acid that encodes for the antibodies described above. Some embodiments provide an isolated polynucleotide encoding an antibody described herein.

A recombinant expression cassette comprising a polynucleotide encoding the antibody of the present invention is also contemplated. The polynucleotide may be under the control of a transcriptional promoter allowing the regulation of the transcription of said polynucleotide in a host cell.

The present invention also provides a recombinant expression cassette comprising a polynucleotide according to the present invention under the control of a transcriptional promoter allowing the regulation of the transcription of said polynucleotide in a host cell. Said polynucleotide can also be linked to appropriate control sequences allowing the regulation of its translation in a host cell.

The present invention also provides a recombinant vector (e.g., a recombinant expression vector) comprising a polynucleotide according to the present invention. Advantageously, said recombinant vector is a recombinant expression vector comprising an expression cassette according to the present invention.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors". Vectors, including expression vectors, comprise the nucleotide sequence encoding for the polypeptides described herein and a heterogeneous sequence necessary for proper propagation of the vector and expression of the encoded polypeptide. The heterogeneous sequence is sequence from a difference species than the polypeptide. The heterologous sequence can comprise a heterologous promoter or heterologous transcriptional regulatory region associated with the nucleic acid of the polypeptide that allows for expression of the polypeptide. As used herein, the terms "heterologous promoter," "promoter," "promoter region," or "promoter sequence" refer generally to transcriptional regulatory regions of a gene, which may be found at the 5' or 3' side of the polynucleotides described herein, or within the coding region of the polynucleotides, or within introns in the polynucleotides. Typically, a promoter is a DNA regulatory region capable of binding RNA polymerase in a cell and initiating transcription of a downstream (3' direction) coding sequence. The typical 5' promoter sequence is bounded at its 3' terminus by the transcription initiation site and extends upstream (5' direction) to include the minimum number of bases or elements necessary to initiate transcription at levels detectable above background. Within the promoter sequence is a transcription initiation site, as well as protein binding domains (consensus sequences) responsible for the binding of RNA polymerase.

The present invention also provides a host cell containing a recombinant expression cassette or a recombinant expression vector according to the present invention. The host cell is either a prokaryotic or eukaryotic host cell. The host cell is capable of expressing the antibodies of the present invention. Suitable host cells include, but are not limited to, mammalian cells and yeast cells. In some embodiments, the host cell may be a eukaryotic cell. The terms "host cell" refers to a cell into which exogenous nucleic acid has been introduced, including the progeny of such cells. Host cells include "transformants" and "transformed cells", which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

The present invention contemplates methods of delivering an agent, for example, but not limited to, a pharmaceutically active or otherwise therapeutic compound to and/or across the blood-brain barrier into a subject's brain. Such a method includes administering a pharmaceutically active or therapeutic compound in combination with a purified BBB-targeting antibody (e.g. scFv4 or scFv40) to a subject such that the antibody directs delivery of the agent to and/or across the blood brain barrier into the subject's brain.

One may wish to administer the BBB-selective antibodies of the present invention without the modifications described above. For example, one may administer the antibodies through an intravenous injection or through intra-peritoneal and subcutaneous methods.

The present disclosure also provides compositions comprising an antibody or antigen-binding fragment thereof specific for BBB as described above. In some embodiments, the composition is a pharmaceutical composition comprising the antibody or antigen-binding fragment thereof specific for BBB and a pharmaceutically acceptable carrier. Compositions are provided that include one or more of the disclosed antibodies that bind BBB. Compositions comprising antibodies that are conjugated to and/or directly or indirectly linked to an agent are also provided. The compositions can be prepared in unit dosaged forms for administration to a subject. The amount and timing of administration are at the discretion of the treating clinician to achieve the desired outcome. The antibody can be formulated for systemic or local (such as intravenous, intrathecal, intra-cranial) administration. In one example, the antibody is formulated for parenteral administration, such as intravenous administration.

As used herein, "pharmaceutical composition" means therapeutically effective amounts of the antibody together with a pharmaceutically-acceptable carrier. "Pharmaceutically acceptable" carriers are known in the art and include, but are not limited to, for example, suitable diluents, preservatives, solubilizers, emulsifiers, liposomes, nanoparticles and adjuvants. Pharmaceutically acceptable carriers are well known to those skilled in the art and include, but are not limited to, 0.01 to 0.1 M and preferably 0.05M phosphate buffer or 0.9% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include isotonic solutions, alcoholic/aqueous solutions, emulsions or suspensions, including saline and buffered media.

Pharmaceutical compositions of the present disclosure may include liquids or lyophilized or otherwise dried formulations and may include diluents of various buffer content (e.g., Tris-HCl, acetate, phosphate), pH and ionic strength, additives such as albumin or gelatin to prevent absorption to surfaces, detergents (e. g., Tween 20, Tween 80, Pluronic F68, bile acid salts), solubilizing agents (e.g., glycerol, polyethylene glycerol), anti-oxidants (e.g., ascorbic acid, sodium metabisulfite), preservatives (e.g., Thimerosal, benzyl alcohol, parabens), bulking substances or tonicity modifiers (e.g., lactose, mannitol), covalent attachment of polymers such as polyethylene glycol to the protein, complexation with metal ions, or incorporation of the material into or onto particulate preparations of polymeric compounds such as polylactic acid, polyglycolic acid, hydrogels, etc, or onto liposomes, microemulsions, micelles, milamellar or multilamellar vesicles, erythrocyte ghosts, or spheroplasts. Such compositions will influence the physical state, solubility, stability, rate of in vivo release, and rate of in vivo clearance. Controlled or sustained release compositions include formulation in lipophilic depots (e.g., fatty acids, waxes, oils).

In some embodiments, the compositions comprise a pharmaceutically acceptable carrier, for example, buffered saline, and the like. The compositions can be sterilized by conventional, well known sterilization techniques. The compositions may contain pharmaceutically acceptable additional substances as required to approximate physiological conditions such as a pH adjusting and buffering agent, toxicity adjusting agents, such as, sodium acetate, sodium chloride, potassium chloride, calcium chloride, sodium lactate, and the like.

In some embodiments, the antibodies are provided in lyophilized form and rehydrated with sterile water or saline solution before administration. In some embodiments, the antibodies are provided in sterile solution of known concentration. In some embodiments, the antibody composition may be added to an infusion bag containing 0.9% sodium chloride, USP and in some cases, administered in a dosage of from 0.5 to 15 mg/kg of body weight.

As used herein "subject" or "patient" refers to mammals and non-mammals. "Mammals" means any member of the class Mammalia including, but not limited to, humans, non-human primates such as chimpanzees and other apes and monkey species: farm animals such as cattle, horses, sheep, goats, and swine: domestic animals such as rabbits, dogs, and cats: laboratory animals including rodents, such as rats, mice, and guinea pigs; and the like. Examples of non-mammals include, but are not limited to, birds, and the like. The term "subject" does not denote a particular age or sex. In one specific embodiment, a subject is a mammal, preferably a human.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, intradermal administration, intrathecal administration and subcutaneous administration. Administration can be continuous or intermittent. In various aspects, a preparation can be administered therapeutically: that is, administered to treat an existing disease or condition. In a preferred embodiment, the administration is intracerebral administration or intravenous administration.

For purposes of the present invention, "treating" or "treatment" describes the management and care of a subject for the purpose of combating the disease, condition, or disorder. Treating includes the administration of an antibody of present invention to prevent the onset of the symptoms or complications, alleviating the symptoms or complications, or eliminating the disease, condition, or disorder.

In some embodiments, kits for carrying out the methods described herein are provided. The kits provided may contain the necessary components with which to carry out one or more of the above-noted methods.

The present invention has been described in terms of one or more preferred embodiments, and it should be appreciated that many equivalents, alternatives, variations, and modifications, aside from those expressly stated, are possible and within the scope of the invention.

It should be apparent to those skilled in the art that many additional modifications beside those already described are possible without departing from the inventive concepts. In interpreting this disclosure, all terms should be interpreted in the broadest possible manner consistent with the context. Variations of the term "comprising" should be interpreted as referring to elements, components, or steps in a non-exclusive manner, so the referenced elements, components, or steps may be combined with other elements, components, or steps that are not expressly referenced. Embodiments referenced as "comprising" certain elements are also contemplated as "consisting essentially of" and "consisting of" those elements. The term "consisting essentially of" and "consisting of" should be interpreted in line with the MPEP and relevant Federal Circuit interpretation. The transitional phrase "consisting essentially of" limits the scope of a claim to the specified materials or steps "and those that do not materially affect the basic and novel characteristic(s)" of the claimed invention. "Consisting of" is a closed term that excludes any element, step or ingredient not specified in the claim. For example, with regard to sequences "consisting of" refers to the sequence listed in the SEQ ID NO. and does refer to larger sequences that may contain the SEQ ID as a portion thereof.

The invention will be more fully understood upon consideration of the following non-limiting examples.

The present invention has been described in terms of one or more preferred embodiments, and it should be appreciated that many equivalents, alternatives, variations, and modifications, aside from those expressly stated, are possible and within the scope of the invention.

The invention will be more fully understood upon consideration of the following non-limiting examples.

Examples

Example 1: Brain Perfusion Screens and Next Generation Sequencing Identified Blood-Brain Barrier Binding Antibodies Antibodies that target the blood-brain barrier (BBB) in vivo are of particular interest for the treatment of neurological diseases. In this example, we screened a phage display single-chain antibody (scFv) library by brain perfusion in an attempt to isolate scFv that target the rat BBB. After four rounds of screening, the resulting antibody pool remained highly complex and discrete clonal sampling did not identify any scFvs capable of binding to the rat BBB. Thus, the heavy chain CDR3 in the resulting pools was subjected to NGS, and the resulting data was used to identify 12 scFv clones that were of high abundance and/or enriched from round 3 to 4, signifying potential hits. Of these, two scFv, denoted scFv 4 and scFv 40, were identified that bound the rat BBB. Neither of these scFvs was identified by discrete sampling, motivating NGS as a tool to identify lead antibodies from complex in vivo screens.

Methods

Phage and Bacteria

The phage display scFv library was a kind gift of Dr. James D. Marks. The library is of human origin and its construction and diversity were previously described[22,23]. The host bacteria strain was TG1 *Escherichia coli* (Agilent Technologies). All infections and phage purifications were performed using standard techniques described previously[4,24] Briefly, infections were performed by static incubation of the phage with log phage TG1 grown in 2×YT media (16 g/L tryptone, 10 g/L yeast extract, and 5 g/L NaCl, pH=7.0) at 37° C. for 30 minutes followed by another incubation with shaking at 37° C. for 30 minutes. Phage were precipitated and purified using polyethylene glycol as a precipitant[24].

Transcardial Perfusion-Based Screen

A transcardial perfusion-based screen was performed in male Sprague-Dawley rats weighing between 220 and 250 grams purchased from Harlan Laboratories (Indianapolis, IN). The hearts of anesthetized rats were exposed and a hemostat was used to clamp the descending aorta after the branch to the carotid artery to direct perfusate flow to the brain. A 22 gauge catheter was inserted into the left ventricle of the heart and connected to a peristaltic pump. A small incision was made in the right atrium of the heart to allow the outflow of blood and perfusate. First a heparinized perfusate (0.9% NaCl, 0.4% $NaNO_2$, 100 units/mL of heparin, and either 0.1% BSA for first three rounds or 1% goat serum for round 4) was perfused at 10 ml/min for 10 minutes to clear blood from the vasculature, then the phage library was perfused using the phage amounts detailed in Table 1 diluted in 10 ml of heparinized saline and perfused at 2 ml/min. Then, the rat vasculature was washed by perfusing 10 mL of heparinized perfusate containing either BSA or goat serum at 2 ml/minute to wash unbound phage from the vasculature.

TABLE 1

Screen progress assessed by phage input and recovery

|  | Round 1 | Round 2 | Round 3 | Round 4-12 | Round 4-11 | Round 4-8 | Round 4-4 |
|---|---|---|---|---|---|---|---|
| Phage Input | $4.5 \times 10^{11}$ | $1.5 \times 10^{12}$ | $1.9 \times 10^{12}$ | $1.5 \times 10^{12}$ | $1.5 \times 10^{11}$ | $1.5 \times 10^{8}$ | $1.5 \times 10^{4}$ |
| Phage Recovered | $7.3 \times 10^{5}$ | $2.4 \times 10^{6}$ | $1.12 \times 10^{7}$ | $5.39 \times 10^{6}$ | $1.0 \times 10^{6}$ | $2.7 \times 10^{4}$ | $4.0 \times 10^{3}$ |
| Fraction Recovered | $1.8 \times 10^{-6}$ | $2.2 \times 10^{-6}$ | $7.8 \times 10^{-6}$ | $4.7 \times 10^{-6}$ | $9.5 \times 10^{-6}$ | $2.3 \times 10^{-4}$ | $4.2 \times 10^{-1}$ |

After perfusion, the rat brain was removed and placed in phosphate buffered saline (PBS, Sigma #D8537) on ice. Subsequently the cerebellum was removed, and the cortices dissected away from the white matter. Each cortex was then homogenized in the presence of 1 mL of lysis buffer (100 mM Triethanolamine in ddH$_2$O) in a Dounce homogenizer. Finally, each homogenate was incubated with 10 ml of log growth phase TG1 *E. Coli* for 30 minutes at 37° C., and then shaken in a rotator for 30 minutes at 37° C. for phage recovery. 100 µL of the infected bacteria was reserved for titering. The remainder was pelleted, resuspended and plated on 10 cm diameter 2×YT plates with 15 µg/ml tetracycline. The plates were incubated at 37° C. overnight. The phage harboring bacteria were recovered and used to inoculate cultures for the next round of selection.

NGS Sample Preparation

Copies of the forward primers designed by D'Angelo et al., 2014[21] for the amplification of human CDR-H3's were ordered from Integrated DNA Technologies (Coralville, IA). They were designed for a common annealing temperature and should prime ~94% of all human framework 3 regions on the variable heavy chain if up to four base mismatches are allowed[21]. We then designed a reverse primer that binds to the conserved linker region with a similar annealing temperature to the forward primers. The sequence was (5' GAA CCG CCT CCA CCT GAG G 3' (SEQ ID NO:29), and the resulting amplicon was expected to be around 150 base pairs.

Phage DNA minipreps were performed on 5 mL overnight cultures of the phage pools to be submitted for sequencing (Round 3, Round 4-4, Round 4-8, Round 4-11, and Round 4-12). PCR was performed on each of these libraries using Platinum Pfx DNA polymerase (Life Technologies #11708-0210) according to the manufacturer instructions for 15 cycles with an annealing temperature of 55° C. The DNA was then run on an agarose gel and the band at ~150 base pairs was isolated and recovered using a gel DNA purification kit (Zymo Research #D4008). The amplicons were then submitted to the University of Wisconsin Biotechnology Center for barcoding and synthesis-based sequencing on an Illumina HiSeq 2500 chip with a 150 base pair readout.

Analysis of NGS Data Using the Antibody Mining Toolbox

Overall quality of the sequence data was assessed by the FastQC program. Detailed quality information can be found in FIGS. 6 and 7. The Antibody Mining Toolbox[21] was used for both read quality filtering and CDR-H3 determination. The raw FASTQ files were individually submitted to the cdr3_pipleline.py script. The quality control and accuracy parameters were left on their default settings with the exception of the minimum read length was set to 150 base pairs. A phred score of 20 for each read was set as the quality cutoff. The file containing the binned CDR-H3 data for each of the pools resulting from the pipeline script was fed to cdr3_cluster.py script. This script uses the binned data from two or more screening rounds and collates the data based on the CDR-H3 sequence. One master file was created that compared all five of the sequenced libraries. This was used for Excel-based enrichment analysis. Four more cluster files were generated using cdr3_cluster.py to compare the round 3 library with each subsequent round 4. These four files were fed to the count_pairs.py script to generate four .csv files containing the data graphed in FIG. 2. Once the binned data was imported to Excel via the output of cdr3_cluster.py, the data was sorted from most abundant to least abundant in Round 3. Then the number of reads for each CDR-H3 in each library was normalized to the total number of accepted reads in each sequenced DNA pool. This "fractional abundance" was used to calculate the fold change enrichment from Round 3 to the various Round pools.

Recovery and Production of scFvs

Twelve CDR-H3's were selected for further analysis. To recover the whole scFv containing these CDR-H3's, a two-step PCR scheme was designed. First, a forward primer was designed that bound specifically to the unique CDR-H3 of interest. The forward primer that primes in the CDR-H3 was used in a PCR reaction with the reverse primer (5'-GAATTTTCTGTATGAGGTTTTGCTAAA-3' (SEQ ID NO:30)) binding to a constant region 3' of the variable light chain sequence in phage backbone. In parallel, the reverse complement of the CDR-H3 primer was used in conjunction with a forward primer (5'-TTTTTGGAGATTTT-CAACGTGA-3' (SEQ ID NO:31)) that binds to the phage backbone 5" to the variable heavy chain encoding region. These two amplicons we gel purified and then assembled in a second PCR reaction using the forward and reverse PCR primers that the vector backbone. The reaction product was again run on a 1% agarose gel and the band that appeared at ~750) base pairs was purified. The assembled product was double digested using the Fast Digest enzymes NcoI and NotI (Life Technologies), according to the manufacturer's instructions and ligated into the similarly cut bacterial expression vector pSYN1 which contains the c-myc and His6 epitope tags. This was then transformed into TG1 bacteria and sanger sequenced to confirm the presence of the correct insert. Soluble scFv were prepared by bacterial expression, periplasmic extraction and HisPur Ni-NTA purification (Thermo Scientific) exactly as previously described[14]. The scFv concentrations were quantified using UV 280 absorbance and extinction coefficients generated by ExPASy (web.expasy.org/protparam/) in conjunction with SDS-PAGE stained with coomassie blue.

ScFv Immunolabeling of Rat Brain Tissue

Rat brains were snap frozen and 7 µm tissue sections were generated. Sections were immunolabeled as previously described[14]. Briefly, sections were thawed and air dried for 20 minutes. Sections were blocked in PBSG (PBS with 40% goat serum) for 30 minutes. ScFvs were artificially dimerized at a concentration of 50 µg/mL in PBSG via the c-myc tag with the monoclonal antibody 9E10 (Fisher Scientific) and incubated on the sections for 30 minutes on ice[12]. After two washes with PBS, sections were incubated with anti-mouse Alexa594 (Life Technologies) and LEA-FITC (Sigma) for 1 hour in PBSG. The sections were washed 3 times in PBS and then fixed for 10 minutes in 4% paraformaldehyde in PBS.

For fresh and unfrozen sections, a vibratome 1000 was used to generate 150 µm thick brain sections. These sections were blocked with 40% goat serum in PBS for 30 minutes. Afterwards, pre-dimerized scFvs at a concentration of 50 µg/mL in PBSG were incubated with the sections for 2.5 hours on ice. The sections were washed three times with PBS and then incubated with anti-mouse Alexa594 (Life Technologies) and LEA-FITC (Sigma) for 1 hour in PBSG. The sections were washed 3 times in PBS and then fixed for 10 minutes in 4% paraformaldehyde in PBS. Fixed sections (frozen or fresh) were washed 3 additional times and mounted with ProLong Gold mounting media containing DAPI (Life Technologies #36935) and a coverslip. The finished slides were visualized on an Olympus fluorescence microscope connected to a Diagnostic Instruments camera run by MetaVue.

Design and Implementation of Brain Perfusion Screen

The nonimmune antibody library used in this study was comprised of human scFvs displayed on the surface of the filamentous phage fd-tet with an estimated diversity of $5 \times 10^8$ scFv clones[22,23,25]. While phage display is a viable option for in vivo screening, phage are quickly scavenged from the blood stream after intravenous administration, resulting in a serum half-life of only 15 minutes in rats[17,26,27]. To combat this problem, we instead implemented a perfusion-based screen in which the phage displayed libraries were transcardially perfused into rat brain by clamping the descending aorta (See FIG. 1 for workflow). This approach also allowed brain vascular sampling of the full library diversity without having to pass through peripheral organs. Prior to the library perfusion, a heparinized saline solution was perfused to clear the circulatory system of blood (See Materials and Methods for details). For the first screening round, $4.5 \times 10^{11}$ colony forming units (cfu) of the library were perfused, followed by a saline wash to limit the non-specific phage remaining in the vasculature. The brain was removed, and the cortex dissected from the cerebellum and white matter. The cortex was mechanically homogenized in triethanolamine-containing lysis buffer and the homogenate used to infect bacteria for phage recovery and expansion. For subsequent rounds, the titers of perfused phage are detailed in Table 1. Initially, four rounds of screening were performed. The titer of phage perfused as well as the amount recovered, and the fraction of the input phage that was recovered can be seen in Table 1. The absolute fractional recovery was quite low as has been observed previously with intravenously administered phage libraries[15], likely a consequence of perfusion rates limiting the interaction of phage with the brain vasculature. However, the amount of phage recovered from round to round follows the expected pattern of low initial recovery in the first round, with two rounds of increasing phage recovery, and finally an attenuation of phage recovery in the fourth round (4-12).

Noting the large number of phage recovered from brain cortices, even after Round 1, where there would likely be few true binders, it was apparent that a high non-specific phage recovery could be a problem for clonal analysis techniques. Thirty-eight random clones from the R4-12 library were selected for sequencing-based analysis. Of 36 insert-containing phage clones sequenced, there were no duplicated clones. These phage recovery and diversity results indicated that the complexity of the library was still very high after 4 rounds of perfusion screening, likely as a result of the high non-specific phage recovery. In an attempt to increase the stringency of the screen and lessen the impact of non-specific phage recovery, Round 4 of screening was repeated with lower numbers of perfused phage (Table 1). These are designated R4-11 ($1.5 \times 10^{11}$ phage), R4-8 ($1.5 \times 10^8$ phage) and R4-4 ($1.5 \times 10^4$ phage) with R4-12 ($1.5 \times 10^{12}$ phage) being the original Round 4. It is significant to note that the lower the input phage titer, the higher the fraction of phage recovered, perhaps suggesting a specific enrichment of BBB binders (Table 1). However, upon sequencing of approximately 30 random clones from each of the new R4 (90 clones total), the libraries were still of high complexity with very few duplicated sequences suggesting that while the fraction of phage recovered was high, the screen background was also high.

NGS Characterization of Library Pools

Figure 1:
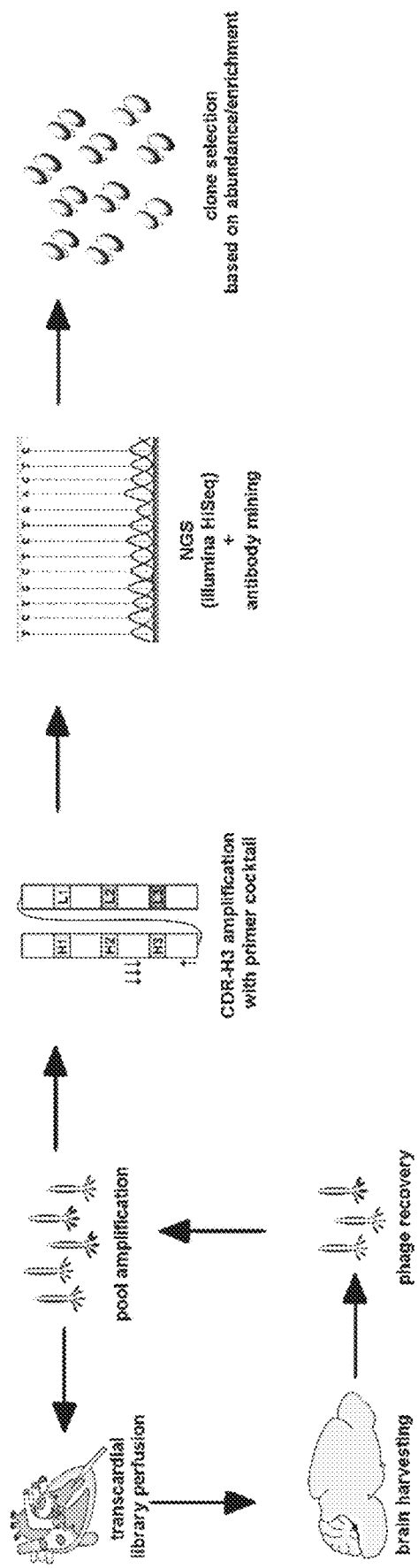
FIG. 1 is a diagram of the brain perfusion screening workflow. Phage display library pools were introduced into brain by transcardial perfusion. Brain tissue was removed, dissected and bound phage recovered. The recovered phage pools were amplified in bacteria and prepped for the next brain perfusion round. A total of four perfusion rounds were performed. NGS was then used to analyze Round 3 and various Round 4 outputs by sequencing CDR-H3 regions. Eighteen forward primers that bind to the various germline sequences in the framework 3 region on the variable heavy chain were used with a single reverse primer that binds to the conserved linker region to amplify the CDR-H3 region of the construct for use in NGS. The CDR-H3 abundance and enrichment were evaluated using the antibody mining toolbox to identify clones with favorable abundance and enrichment patterns. These clones were produced and assessed for brain tissue binding.
Figure 6:
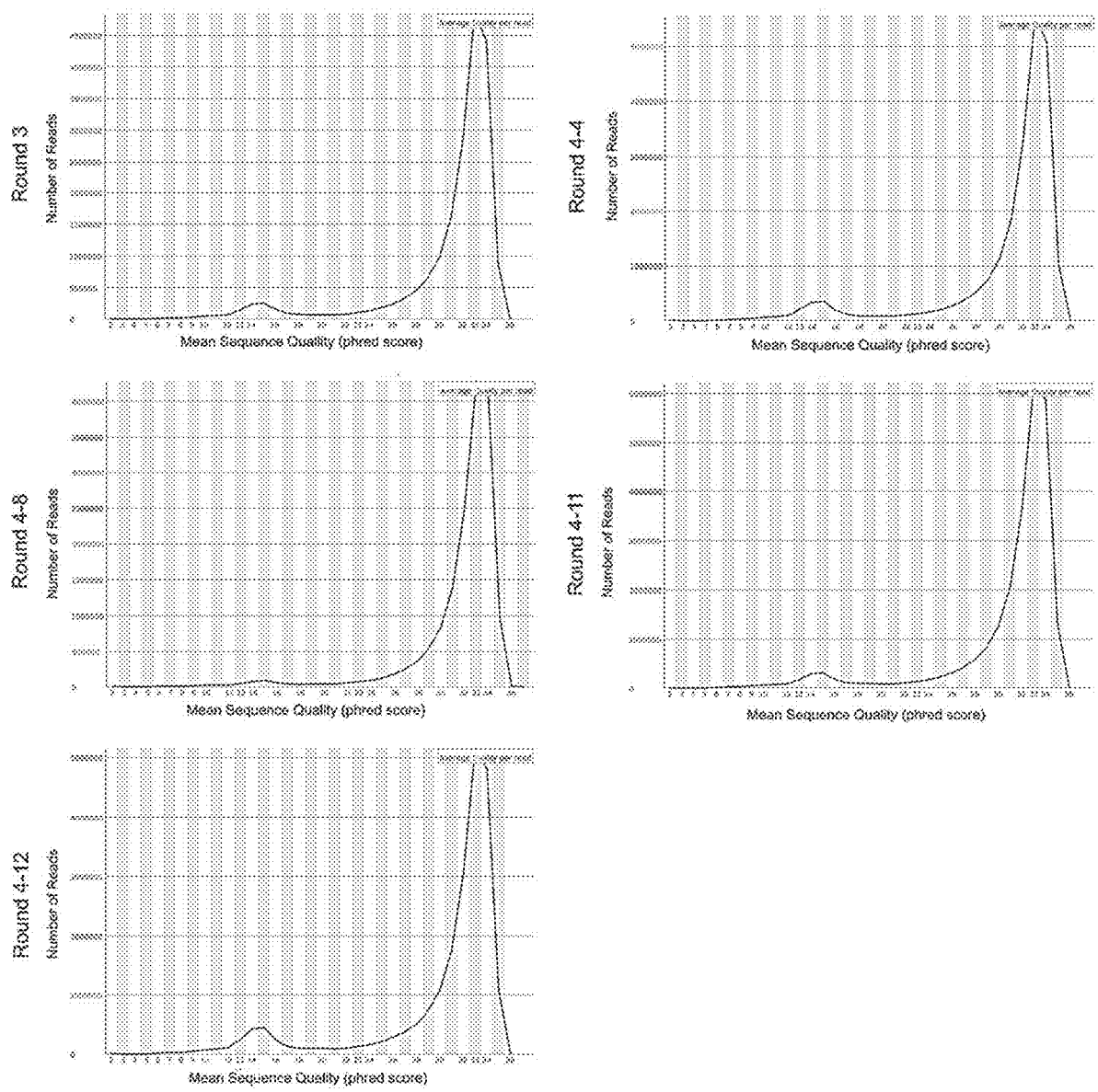
FIG. 6 shows NGS sequencing read quality. The number of sequencing reads and their associated average phred quality score across the whole read is shown for each Round 3 and Round 4 pool. The primary peaks occur at a phred score of ~33 for all pools, while a minor peak observed with a phred score of ~15.
Figure 7:
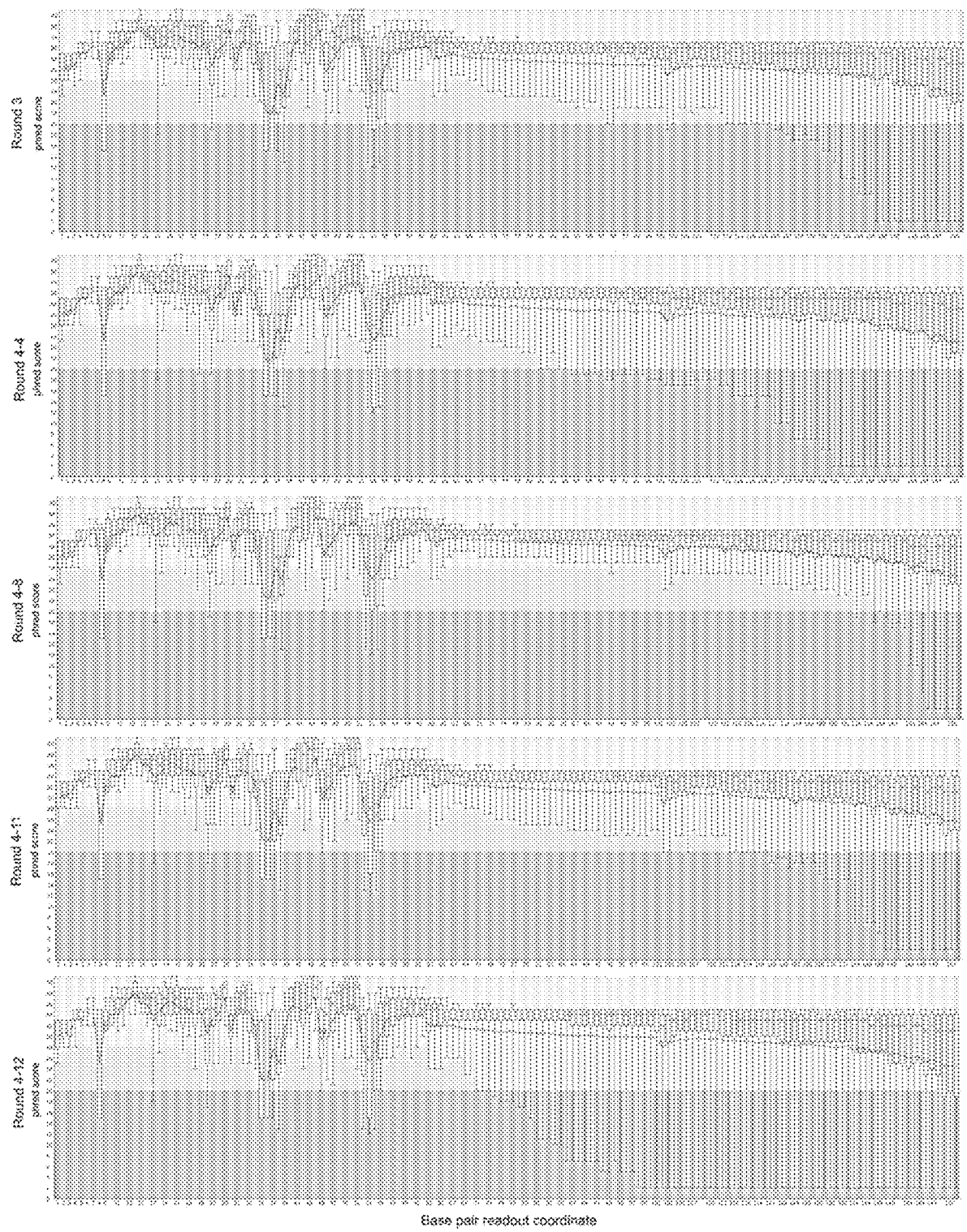
FIG. 7 shows the average phred score on a per base basis. The average phred score for each Round 3 and Round 4 is shown on a per base basis. The red shaded area is a score of <20, 20<yellow<28, and green is >28. The blue line represents the score mean, the red line represents the score median, the yellow box represents the inner 50% of reads (from 25% to 75%), and the barred lines represent the inner 80% (from 10% to 90%).

To better explore the sequence diversity in the various pools and identify particular antibody clones that may warrant further investigation, NGS was used. Since the heavy chain CDR3 (CDR-H3) can often be used as representative of the antigen binding specificity of the scFv[28], we sequenced CDR-H3 as a proxy for tracking an individual scFv from round to round. A previously described set of 18 forward primers that target the third variable heavy chain framework region in human antibody germline sequences[21] was used along with a reverse primer in the conserved sequence of the $(Gly_4-Ser)_3$ linker (FIG. 1). This suite of primers was used in multiplex PCR reactions to amplify the CDR-H3's from the Round 3 pool and all of the subsequent Round 4 pools. Each of these pools of amplicons was barcoded and sequenced using the Illumina HiSeq2500 platform, with enough reads to oversample all of the estimated diversity within each pool. The overall quality of the sequencing run along with the per base quality for each barcoded pool submitted was analyzed. The majority of the sequencing reads had an average phred score between 28 and 36 (FIG. 6). The average phred score at each base position was above 20 for each pool, and was above 28 at most positions along the 150 base read indicating sequencing runs of acceptable quality (FIG. 7).

Figure 2:
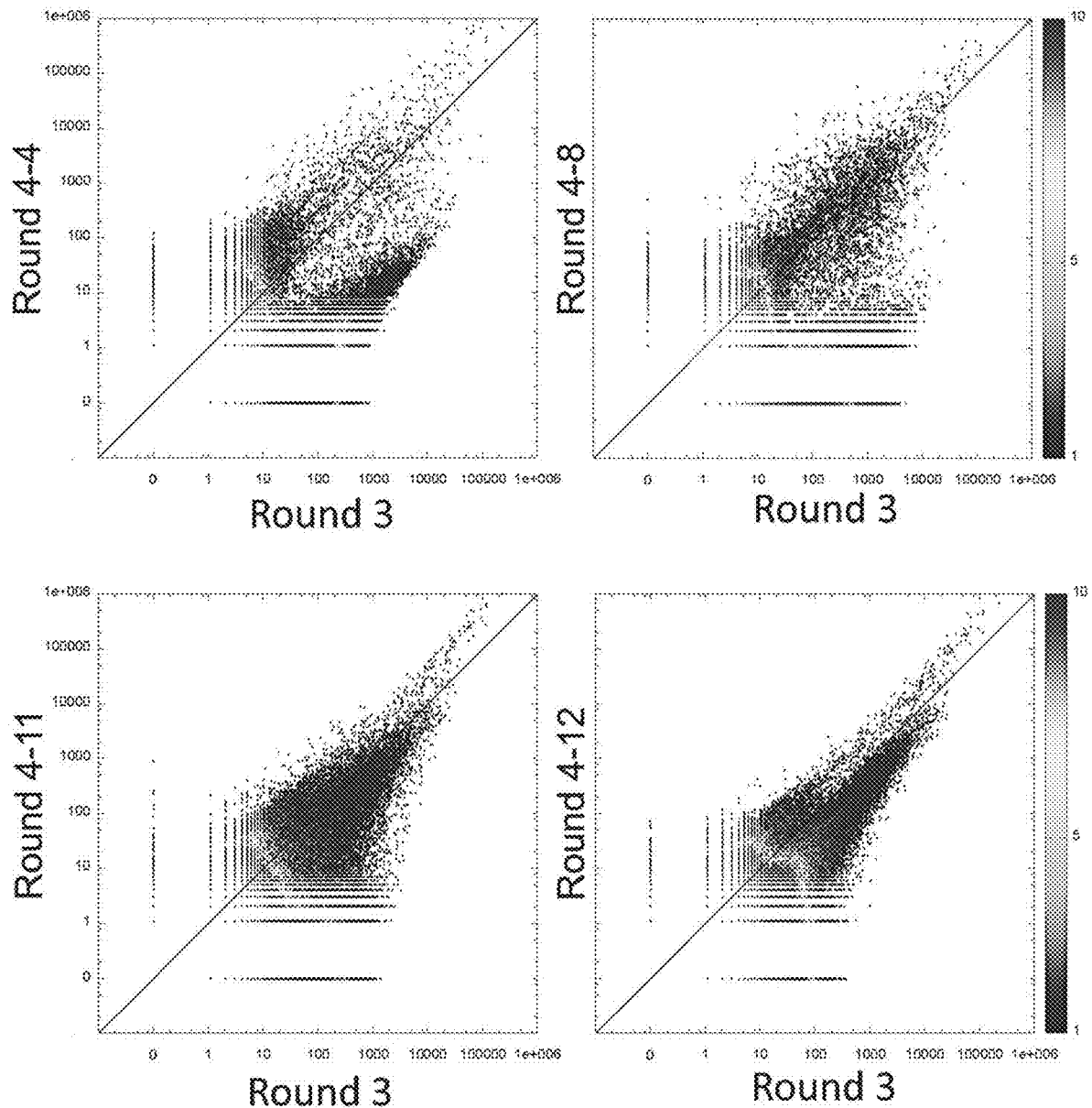
FIG. 2 shows comparison of NGS data between screening rounds. The number of sequencing reads for each individual CDR-H3 in the Round 3 pool is compared to each Round 4 pool. The color gradient represents the number of unique CDR-H3's that possess that number of reads (e.g. red is 10 or greater CDR-H3s, purple is 1 CDR-H3). It should also be noted that the data points in the lower left of each graph most likely represent the errors in base calls, or errors due to PCR amplification.

Next, the cdr3_pipline script from the antibody mining toolbox[21] was used to exclude reads with an average phred score of less than 20, as well as to identify CDR-H3's. The number of usable reads comprised >74% of the total reads for each pool (Table 2). The cdr3 pipline script identifies CDR-H3's by keying on conserved sequences surrounding CDR-H3; namely, the cysteine that appears before the CDR-H3 and the tryptophan that appears after each CDR-H3. The total number of unique CDR-H3's discovered across all libraries was $5.9 \times 10^6$. The number of unique CDR-H3's found in each pool decreased somewhat with the decreasing amount of phage input, but the overall numbers remained high and ruled out any possibility of even marginally comprehensive discrete sampling. Next, to compare how each Round 4 pool compared to the Round 3 parent pool, the number of reads for each CDR-H3 in the Round 3 pool were compared to that in each Round 4 pool. On a pool-wide basis, there was clear similarity between the Round 3 and Round 4 pools (FIG. 2). Divergence from the Round 3 pool was more substantial as the input phage titer in the screen was reduced (correlation coefficients: Round 4-4=0.40, Round 4-8=0.65, Round 4-11-0.82, and Round 4-12=0.81), suggestive of a benefit in screen stringency with reduced input titer. In addition, each Round 4 pool also exhibited an enriching tail of transcripts at high abundance. These could potentially represent binding scFv clones or alternatively, those that drive a phage growth bias, allowing their non-specific enrichment from round to round.

TABLE 2

Next generation quality control overview

| Library | Usable Reads | Total Reads | % Sequence Accepted | Unique CDR-H3 |
|---|---|---|---|---|
| Round 3 | $1.6 \times 10^7$ | $1.9 \times 10^7$ | 81.6 | $3.28 \times 10^5$ |
| Round 4-12 | $1.6 \times 10^7$ | $2.2 \times 10^7$ | 74.3 | $1.86 \times 10^5$ |
| Round 4-11 | $2.0 \times 10^7$ | $2.5 \times 10^7$ | 79.7 | $1.63 \times 10^5$ |
| Round 4-8 | $1.4 \times 10^7$ | $1.7 \times 10^7$ | 84.2 | $1.06 \times 10^5$ |
| Round 4-4 | $1.7 \times 10^7$ | $2.3 \times 10^7$ | 76.2 | $8.60 \times 10^4$ |

Figure 3:
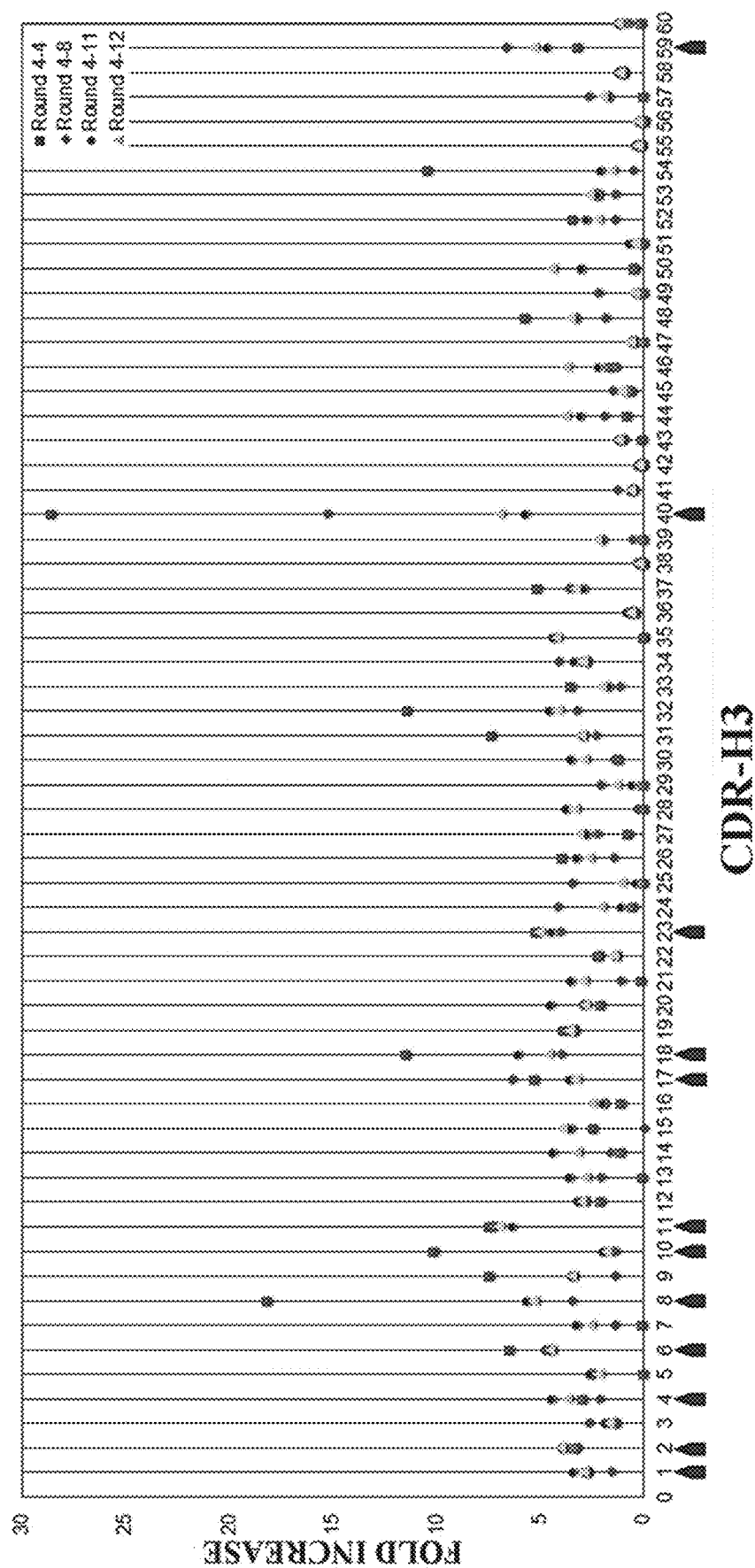
FIG. 3 demonstrates the analysis of CDR-H3 abundance and enrichment. The Round 3 to Round 4 enrichments for the 60 most abundant CDR-H3s are presented as fold increase for each Round 4 pool as denoted in the inset legend. Clones are arranged from most to least abundant in the Round 3 pool (1 to 60). The red wedges denote the CDR-H3s that were selected for further analysis.
Figure 4:
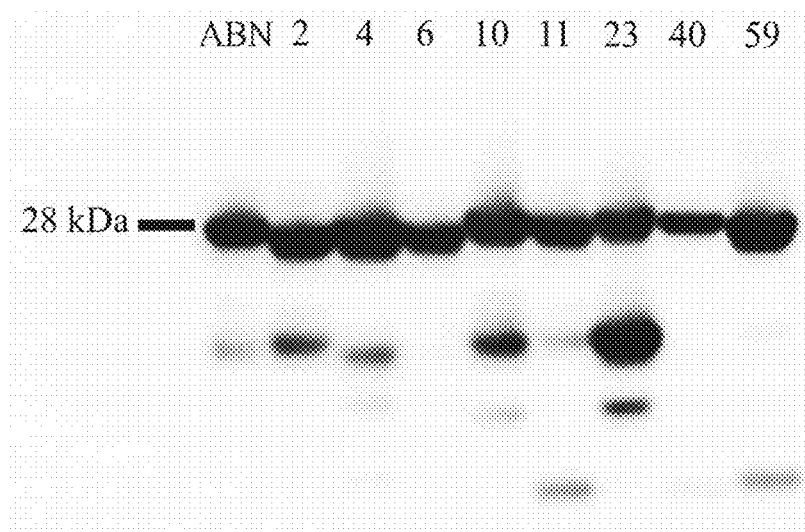
FIG. 4 demonstrates the expression of scFv clones. ScFv clones were expressed and purified from bacterial lysates as described in the methods section and normalized for total protein concentration. Western blotting for the epitope tag using an anti-c-myc antibody was then used to assay for protein production. ScFv clones are listed by their abundance number and ABN is a negative control scFv that recognizes botulinum neurotoxin. The primary scFv band was found at ~28 kDa at the expected size of the intact scFv, with the smaller bands likely being unpaired variable chains and other truncated products.

In order to select individual CDR-H3's from the various pools for further analysis, two criteria were evaluated: Abundance within each pool, and fold change from round 3 to round 4. The cdr3_cluster script was used to compare all of pools associating the CDR-H3 amino acid sequence with its abundance in each pool, and the data was then sorted according to number of reads in Round 3 (FIG. 3). For a successful screen, one would expect to see high abundance and high enrichment clones exhibit rat BBB binding. Therefore, a subset of CDR-H3's that satisfied these criteria were selected for further analysis (FIG. 3). Twelve clones were selected that were of high abundance and enriched in each Round 4 screen. Clones 8 and 10 were selected as examples where the potentially more stringent Round 4-4 screen exhibited an enhanced enrichment. The selected CDR-H3 sequences and associated NGS data can be found in Table 3. It is interesting to note that even though the selected clones were present in the various Round 4 pools at an abundance ranging between ~0.5% and 5% of each population, only clones 2, 6, 10 and 11 were also found in the 128 clones that were randomly chosen and individually sequenced from the Round 4 pools.

from each CDR-H3 based PCR recovery process were sequenced. In all 12 cases, at least one transformant had the exact CDR-H3 sequence that appeared in the NGS analysis, and these clones were used for scFv production and purification. Of the twelve scFvs, only 8 expressed at suitable levels for binding analysis (scFvs 2, 4, 6, 10, 11, 23, 40 and 59) (FIG. 4).

To determine if any of the selected scFvs bound to the rat BBB, scFvs were used to immunolabel either fresh frozen brain tissue sections (FIG. 5) or fresh, never frozen, vibratome cut rat brain tissue to ensure that antigens were not disrupted by processing since the screen was performed with living tissue (FIG. 8). Of the 8 scFvs tested, 6 (scFvs 2, 6, 10, 11, 23, 59) did not exhibit binding to the rat BBB in either brain tissue section format. However, 2 scFvs (4 and 40) clearly bound antigens in rat brain in both frozen and fresh brain tissue sections (FIG. 5 and FIG. 8). ScFv 40 bound specifically to brain microvessels with continuous vessel labeling pattern similar to that of the anti-transferrin receptor antibody. OX26. However, unlike OX26 labeling which can be found throughout the brain, scFv 40) labeling was found only in small ventral brain regions, and infrequently appeared elsewhere throughout the brain cortex. In contrast to scFv 40, scFv 4 bound to both brain microvessels and to extended cellular processes that wrapped brain blood vessels, likely astrocytes (FIG. 5 and FIG. 8). Also, scFv4 binding could be observed throughout the brain. These two scFvs were not identified in the discrete sampling of 128 clones noted above, indicating the value of combining NGS with clonal evaluation.

In this Example, we sought to identify rat BBB targeting scFv using in vivo phage display methods. While in vivo screens represent the highest likelihood for discovery of novel brain targeting molecules, these screens have had limited success, likely because of inherently high background. Indeed, we observed a high background of non-specific phage accumulation that made discrete sampling of potential brain targeting scFvs infeasible. However, NGS was used to address this issue and identify scFvs that were enriched by screening round to round and that spanned a spectrum of abundance. These approaches resulted in the

TABLE 3

Summary table for selected scFv clones

| Clone | CDR-H3 | % of R3 | % of R4-4 | % of R4-8 | % of R4-11 | % of R4-12 | Expressed | BBB Bind |
|---|---|---|---|---|---|---|---|---|
| 1 | GALQSGSYYPPGY (SEQ ID NO: 32) | 1.59 | 4.29 | 2.50 | 5.46 | 4.60 | − | − |
| 2 | DNGEY (SEQ ID NO: 33) | 0.83 | 2.78 | 2.69 | 3.30 | 3.35 | + | − |
| 4 | AWDSYSRKPDY (SEQ ID NO: 4) | 0.81 | 2.42 | 1.77 | 3.64 | 3.01 | + | + |
| 6 | ADGGNSDY (SEQ ID NO: 34) | 0.66 | 4.25 | 3.17 | 2.96 | 2.96 | + | − |
| 8 | GSMVRGPYPRFDP (SEQ ID NO: 35) | 0.48 | 8.75 | 1.67 | 2.74 | 2.55 | − | − |
| 10 | ETGAYYYGMDV (SEQ ID NO: 36) | 0.48 | 4.84 | 0.68 | 0.95 | 0.86 | + | − |
| 11 | DRWLQNWERPFDY (SEQ ID NO: 37) | 0.43 | 3.24 | 3.16 | 2.77 | 3.05 | + | − |
| 17 | YYYDSSAFMTGN (SEQ ID NO: 38) | 0.37 | 1.97 | 2.40 | 1.34 | 1.24 | − | − |
| 18 | DLYDSSGNLHGNWFDP (SEQ ID NO: 39) | 0.36 | 4.16 | 1.45 | 2.20 | 1.69 | − | − |
| 23 | DLHLSIAAAGTGVFKTPLRDY (SEQ ID NO: 40) | 0.26 | 1.37 | 1.06 | 1.17 | 1.31 | + | − |
| 40 | LHSEDSSGWGVFDI (SEQ ID NO: 11) | 0.17 | 4.98 | 2.66 | 1.00 | 1.22 | + | + |
| 59 | RLGYSAPGDY (SEQ ID NO: 41) | 0.13 | 0.42 | 0.87 | 0.61 | 0.69 | + | − |

Recovery, Production and Analysis of Selected scFvs

To recover the entire scFv coding region that is associated with each CDR-H3, primers designed specifically for each CDR-H3 were used to PCR amplify each of the 12 selected scFvs. The open reading frames were subsequently cloned into a bacterial expression vector for production as soluble scFvs. Four individual bacterial transformants resulting identification of scFv 4 (SEQ ID NO:1) and scFv 40 (SEQ ID NO:8) that bind to the rat BBB.

The use of NGS to follow the progress of combinatorial screening efforts is becoming more widely utilized[29,30]. Traditionally, it has been very difficult to track round-by-round clonal enrichment during a screen without substantial cost and effort. NGS now enables the monitoring of individual sequences across a screen at a combinatorial level, ultimately aiding in the assessment and success of the screen[20]. In our case. NGS allowed the intelligent selection of specific scFv clones for downstream phenotypic analysis. Often when NGS is applied to combinatorial screens such as antibody affinity maturation, the most abundant sequences are often those with the most desirable properties, and NGS assures that random sampling of clones will not miss these desirable clones. For example, scFv 4 was abundant in our screen, but was not sampled in 128 randomly picked scFvs. However, some of the most abundant clones such as scFv2 did not bind the rat BBB. Thus, NGS also allows researchers to navigate the high background of an in vivo phage display screen to examine clones that may be much lower in abundance, but that are still enriching from round to round. For example, scFv 40 was a clone that enriched from Round 3 to Round 4 but had a comparatively low abundance that also was not observed in the randomly picked clones. It is also important to note that we did not sample the library diversity comprehensively, but assayed the scFv that, in our estimation, represented the highest likelihood of binding to the BBB. Thus, it is likely that phenotypically interesting scFvs may be in the pools at lower abundance. One approach to identify additional scFvs may be to further mine the NGS data exploring scFvs lower on the abundance scale than just the top 60 most represented CDR-H3's analyzed here, and selecting those that display the most significant fold change between Round 3 and the various Round 4 screens.

To our knowledge scFv 4 and scFv 40 are the first BBB binding antibody fragments to have been recovered from an in vivo screen. While there are a variety of approaches to screen for targeting antibodies, in vivo phage display can be a powerful approach to target relevant antigens in their natural cellular and structural environment. For instance, it has been shown that an antibody which may bind in vitro, may not work well in vivo if the specific epitope is too close to the cell surface as to be sterically inaccessible[31,32] Given the nature of the perfusion screen and limited contact time between phage and the BBB, the scFv binders are likely not additionally filtered for their endocytosis or transcytosis capacity. However, it has been shown that a subset of scFvs isolated in BBB binding screens can also endocytose into brain endothelial cells[12]. Thus, if one were to further examine the BBB binding repertoire described here (scFv 4, scFv 40 others in FIG. 3), it is likely that a subset of scFvs with trafficking properties would be identified. In conclusion, historically difficult in vivo phage display screens can be combined with NGS and data mining tools to identify new targeting antibodies against the accessible BBB proteome.

REFERENCES

1. Stutz C, Zhang X, Shusta E. Combinatorial approaches for the identification of bran drug delivery targets. *Current Pharmaceutical Design*. 2014:20(10): 1564-1576.
2. Goulatis L I, Shusta E V. Protein engineering approaches for regulating blood-brain barrier transcytosis. *Current opinion in structural biology*. 2017:45:109-115.
3. Yu Y J, Zhang Y, Kenrick M, et al. Boosting brain uptake of a therapeutic antibody by reducing its affinity for a transcytosis target. *Science Translational Medicine*. 2011: 3(84).
4. Boado R J, Zhang Y F, Zhang Y, Pardridge W M. Humanization of anti-human insulin receptor antibody for drug targeting across the human blood-brain barrier. *Biotechnology and Bioengineering*. 2007:96(2): 381-391.
5. Zuchero Y J, Chen X, Bien-Ly N, et al. Discovery of Novel Blood-Brain Barrier Targets to Enhance Brain Uptake of Therapeutic Antibodies. *Neuron*. 2016:89(1): 70-82.
6. Enerson B E, Drewes L R. The rat blood-brain barrier transcriptome. *Journal of Cerebral Blood Flow and Metabolism*. 2006; 26(7): 959-973.
7. Daneman R, Zhou L, Agalliu D, Cahoy J D, Kaushal A, Barres B A. The mouse blood-brain barrier transcriptome: A new resource for understanding the development and function of brain endothelial cells. *Plos One*. 2010:5(10).
8. Muruganandam A, Tanha J, Narang S, Stanimirovic D. Selection of phage-displayed llama single-domain antibodies that transmigrate across human blood-brain barrier endothelium. *FASEB Journal*. 2001:15(14):240.
9. Abulrob A, Sprong H, Henegouwen P, Stanimirovic D. The blood-brain barrier transmigrating single domain antibody: mechanisms of transport and antigenic epitopes in human brain endothelial cells. *Journal of Neurochemistry*. 2005:95(4): 1201-1214.
10. Farrington G K, Caram-Salas N, Haqqani A S, et al. A novel platform for engineering blood-brain barrier-crossing bispecific biologics. *FASEB Journal*. 2014:28(11): 4764-4778.
11. Helms H C, Abbott N J, Burek M, et al. In vitro models of the blood-brain barrier: An overview of commonly used brain endothelial cell culture models and guidelines for their use. *Journal of Cerebral Blood Flow and Metabolism*. 2016:36(5): 862-890.
12. Wang X X, Cho Y K, Shusta E V. Mining a yeast library for brain endothelial cell-binding antibodies. *Nature Methods*. 2007:4(2): 143-145.
13. Zhang X, Wang X X, Shusta E V. Creation and Evaluation of a Single-chain Antibody Tetramer that Targets Brain Endothelial Cells. *AIChE Journal*. 2014:60(4): 1245-1252.
14. Jones A, Stutz C, Zhou Y, Marks J, Shusta E. Identifying blood-brain barrier selective single-chain antibody fragments. *Biotechnology Journal*. 2014:5:664-674.
15. Pasqualini R, Ruoslahti E. Organ targeting in vivo using phage display peptide libraries. *Nature*. 1996:380(6572): 364-366.
16. Urich E, Schmucki R, Ruderisch N, et al. Cargo Delivery into the Brain by in vivo identified Transport Peptides. *Scientific Reports*. 2015:5:14104.
17. Roodink I, Franssen M, Zuidscherwoude M, et al. Isolation of targeting nanobodies against co-opted tumor vasculature. *Laboratory Investigation*. 2010:90(1):61-67.
18. Niedringhaus T P, Milanova D, Kerby M B, Snyder M P, Barron A E. Landscape of next-generation sequencing technologies. *Analytical Chemistry*. 2011:83(12): 4327-4341.
19. Georgiou G, Ippolito G C, Beausang J, Busse C E, Wardemann H, Quake S R. The promise and challenge of high-throughput sequencing of the antibody repertoire. *Nature Biotechnology*. 2014:32(2): 158-168.
20. Ravn U, Didelot G, Venet S, et al. Deep sequencing of phage display libraries to support antibody discovery. *Methods*. 2013:60(1):99-110.
21. D'Angelo S, Glanville J, Ferrara F, et al. The antibody mining toolbox: An open source tool for the rapid analysis of antibody repertoires. *Mabs*. 2014:6(1): 160-172.
22. O'Connell D, Becerril B, Roy-Burman A, Daws M, Marks J D. Phage versus phagemid libraries for generation of human monoclonal antibodies. *Journal of Molecular Biology*. 2002:321(1):49-56.

23. Sheets M D, Amersdorfer P, Finnern R, et al. Efficient construction of a large nonimmune phage antibody library: The production of high-affinity human single-chain antibodies to protein antigens. *Proceedings of the National Academy of Sciences of the United States of America.* 1998:95(11):6157-6162.
24. Zhou Y, Marks JD. Identification of target and function specific antibodies for effective drug delivery. In: Dimitrov A, ed. *Therapeutic Antibodies: Methods and Protocols.* Totowa: Humana Press: 2009:145-160.
25. Poul M A, Becerril B, Nielsen U B, Morisson P, Marks J D. Selection of tumor-specific internalizing human antibodies from phage libraries. *Journal of Molecular Biology.* 2000:301(5): 1149-1161.
26. Chen Y H, Chang M, Davidson B L. Molecular signatures of disease brain endothelia provide new sites for CNS-directed enzyme therapy. *Nat Med.* 2009:15(10): 1215-U1145.
27. Valadon P, Garnett J D, Testa J E, Bauerle M, Oh P, Schnitzer J E. Screening phage display libraries for organ-specific vascular immunotargeting in vivo. *Proceedings of the National Academy of Sciences of the United States of America.* 2006:103(2):407-412.
28. Xu J L, Davis M M. Diversity in the CDR3 region of V-H is sufficient for most antibody specificities. *Immunity.* 2000: 13(1):37-45.
29. Hu D, Hu S, Wan W, et al. Effective Optimization of Antibody Affinity by Phage Display Integrated with High-Throughput DNA Synthesis and Sequencing Technologies. *PLOS One.* 2015; 10(6).
30. Hemadou A, Giudicelli V, Smith M L, et al. Pacific Biosciences Sequencing and IMGT/HighV-QUEST Analysis of Full-Length Single Chain Fragment Variable from an In Vivo Selected Phage-Display Combinatorial Library. *Frontiers in immunology.* 2017; 8:1796.
31. Jones A R, Shusta E V. Blood-brain barrier transport of therapeutics via receptor-mediation. *Pharmaceutical Research.* 2007; 24(9): 1759-1771.
32. Muro S. Challenges in design and characterization of ligand-targeted drug delivery systems. *Journal of Controlled Release.* 2012; 164(2): 125-137.

Each publication, patent, and patent publication cited in this disclosure is incorporated in reference herein in its entirety. The present invention is not intended to be limited to the foregoing examples, but encompasses all such modifications and variations as come within the scope of the appended claims.

SEQUENCE LISTING

The application includes the sequences listed within the specification.

```
scFv4 AA:
                                                  (SEQ ID NO: 1)
QVQLVESGGGLVQPGGSLRLSCAASGFTFSSYAMSWVRQAPGKGLE
WVSAIGGSGGSTYYTESVKGRFTISRDNSKNTLYLQMNSLRAEDTAVYYCAKAWDS
YSRKPDYWGQGTLVTVSSGGGGSGGGGSGGGGSNFMLTQDPAVSVALGQTVRITC
QGDSLKSHYASWYHQKPGQAPLLVIYDNNNRPSGVPDRFSGSRSGTSASLAITGVQA
EDEADYYCQSYDSSLRGSRVFGTGTKVTVL scFv4CDRH1 AA - SEQ ID NO: 2 GFTFSSYA (bold)

scFv4 CDRH2 AA - SEQ ID NO: 3 IGGSGGST (italic)

scFv4 CDRH3 AA - SEQ ID NO: 4 AWDSYSRKPDY (underline)

scFv4 CDRL1 AA - SEQ ID NO: 5 SLKSHY (bold/underline)

scFv4 CDRL2 AA - SEQ ID NO: 6 DNN (underline/italic)

scFv4 CDRL3 AA - SEQ ID NO: 7 QSYDSSLRGSRV (bold/italic)

svFv40AA:
                                                  (SEQ ID NO: 8)
QVQLQESGGGLVQAGGSLRLSCAASGFTFSSYGMSWVRLAPGKGLE
WVSAISGSGRSTNYADSVKGRFTIFRDNSKNTLYLQMNSLRAEDTAVYYCAKLHSED
SSGWRVFDIWGQGTMVTVSSGGGGSGGGGSGGGRSQPELTQDPAVSGSPGQSITISY
TGTSSDVGGYNYVSWYQQHPGKAPKLMIYEVSNRPSGVSNRFSGSKSGNTASLTISG
LQAEDEADYYCSSYTDSNVVFGGGTKLTVLG svFv40 CDRH1 AA - SEQ ID NO: 9 - GFTFSSYG (bold)

svFv40 CDRH2 AA - SEQ ID NO: 10 - ISGSGRST (italic)

svFv40 CDRH3 AA - SEQ ID NO: 11 LHSEDSSGWRVFD (underline)

svFv40 CDRL1 AA - SEQ ID NO: 12 - SSDVGGYNY (bold/underline)

svFv40 CDRL2 AA - SEQ ID NO: 13 - EVS (underline/italic svFv40 CDRL3 AA - SEQ ID NO: 14 - SSYTDSNVV (bold/italic)

scFv4: DNA:
                                                  (SEQ ID NO: 15)
CAGGTGCAGCTGGTGGAGTCTGGGGGAGGCTTGGTACAGCCTGGG
GGGTCCCTGAGACTCTCCTGTGCAGCCTCTGGATTCACCTTTAGCAGCTATGCC
ATGAGCTGGGTCCGCCAGGCTCCAGGGAAGGGGCTGGAGTGGGTCTCAGCTATTG
GTGGTAGTGGTGGTAGCACATACTACACAGAGTCCGTGAAGGGCCGGTTCACCAT
CTCCAGAGACAATTCCAAGAACACGCTGTATCTGCAAATGAACAGCCTGAGAGC
CGAGGACACGGCCGTATATTACTGTGCGAAAGCCTGGGATTCGTATAGTAGGAA
```

-continued

ACCTGACTACTGGGGCCAGGGCACCCTGGTCACCGTCTCCTCAGGTGGAGGCGG
TTCAGGCGGAGGTGGCTCTGGCGGTGGCGGATCGAATTTTATGCTGACTCAGGAC
CCTGCTGTGTCTGTGGCCTTGGGACAGACAGTCAGGATCACATGCCAAGGAGAC
AGCCTCAAAAGCCATTATGCAAGCTGGTACCATCAGAAGCCAGGACAGGCCCC
TCTACTTGTCATCTAT*GATAACAAC*AATCGGCCCTCAGGGGTCCCTGACCGATTCT
CTGGCTCCAGGTCTGGCACCTCAGCCTCCCTGGCCATCACTGGGGTCCAGGCTGA
AGATGAGGCTGACTATTACTGC***CAGTCATATGACAGCAGCCTGAGGGGTTCGAGG
GTC***TTCGGAACTGGGACCAAGGTCACCGTCCTAGT scFv4CDRH1 DNA - SEQ ID NO: 16 - GGATTCACCTTTAGCAGCTATGCC
(bold)

scFv4 CDRH2 DNA - SEQ ID NO: 17 - ATTGGTGGTAGTGGTGGTAGCACA
(italic)

scFv4 CDRH3 DNA - SEQ ID NO: 18 - GCGAAAGCCTGGGATTCGTATAGT
AGGAAACCTGACTAC (underline)

scFv4 CDRL1 DNA - SEQ ID NO: 19 - AGCCTCAAAAGCCATTAT
(bold/underline)

scFv4 CDRL2 DNA - SEQ ID NO: 20 GATAACAAC (underline/italic)

scFv4 CDRL3 DNA - SEQ ID NO: 21 -
CAGTCATATGACAGCAGCCTGAGGGGTTCGAGGGTC (bold/italic)

scFv40: DNA:
(SEQ ID NO: 22)
CAGGTGCAGCTGCAGGAGTCGGGGGGAGGCTTGGTACAGGCGGGG
GGGTCCCTCAGACTCTCCTGTGCAGCCTCTGGATTCACCTTTAGCAGCTATGGC
ATGAGCTGGGTCCGCCTGGCTCCGGGGAAGGGGCTGGAGTGGGTCTCAGCT*ATTA
GTGGTAGTGGACGTAGCACA*AACTACGCAGACTCCGTGAAGGGCCGGTTCACCAT
CTTCAGAGACAATTCCAAGAACACGCTGTATCTGCAAATGAACAGCCTGAGAGC
CGAGGACACGGCCGTATATTACTGTGCGAAACTCCATAGTGAGGATAGCAGTGG
CTGGAGAGTTTTTGATATCTGGGGCCAAGGGACAATGGTCACCGTCTCTTCAGGT
GGAGGCGGTTCAGGCGGAGGTGGCTCTGGCGGTGGCAGATCGCAGCCTGAGCTG
ACTCAGGACCCTGCTGTGTCTGGGTCTCCTGGACAGTCGATCACCATCTCCTACA
CTGGAACCAGCAGTGACGTTGGTGGTTATAACTATGTCTCCTGGTACCAACAG
CACCCAGGCAAAGCCCCCAAACTCATGATTTAT*GAGGTCAGT*AATCGGCCCTCAG
GGGTTTCTAATCGCTTCTCTGGCTCCAAGTCTGGCAACACGGCCTCCCTGACCAT
CTCTGGGCTCCAGGCTGAGGACGAGGCTGATTATTACTGC***AGCTCATATACAGAC
AGCAATGTGGTA***TTCGGCGGAGGGACCAAGCTGACCGTCCTAGGT scFv40 CDRH1 DNA - SEQ ID NO: 23 -
GGATTCACCTTTAGCAGCTATGGC (bold)

scFv40 CDRH2 DNA SEQ ID NO: 24 -
ATTAGTGGTAGTGGACGTAGCACA (italic)

scFv40 CDRH3 DNA - SEQ ID NO: 25 -
GCGAAACTCCATAGTGAGGATAGCAGTGGCTGGAGAGTTTTTGAT (underline)

scFv40 CDRL1 DNA - SEQ ID NO: 26 -
AGCAGTGACGTTGGTGGTTATAACTAT (underline/bold)

scFv40 CDRL2 DNA - SEQ ID NO: 27 -
GAGGTCAGT (italic/underline)

scFv40 CDRL3 DNA - SEQ ID NO: 28 -
AGCTCATATACAGACAGCAATGTGGTA (bold/italic)

---

The invention claimed is:

1. An isolated blood brain barrier (BBB)-selective antibody or antigen-binding fragment thereof comprising
   (a) a heavy chain variable domain comprising a CDRH1 region consisting of SEQ ID NO:2, a CDRH2 region consisting of SEQ ID NO:3, and a CDRH3 region consisting of SEQ ID NO:4 and a light chain variable domain comprising a CDRL1 region consisting of SEQ ID NO:5, a CDRL2 region consisting of SEQ ID NO:6, and a CDRL3 region consisting of SEQ ID NO:7, or
   (b) a heavy chain variable domain comprising a CDRH1 region of SEQ ID NO:9, a CDRH2 region consisting of SEQ ID NO:10, and a CDRH3 region consisting of SEQ ID NO:11 and a light chain variable domain comprising a CDRL1 region consisting of SEQ ID NO: 12, a CDRL2 region consisting of SEQ ID NO:13, and a CDRL3 region consisting of SEQ ID NO:14.

2. The BBB-selective antibody or antigen-binding fragment thereof of claim 1, wherein the antibody or antigen-binding fragment thereof is engrafted within a full IgG scaffold of human or other species origin or a single-chain variable fragment (scFv) scaffold of human or other species of origin.

3. The BBB-selective antibody or antigen-binding fragment thereof of claim 1, wherein the antibody comprises SEQ ID NO: 1 or SEQ ID NO:8.

4. The BBB-selective antibody or antigen-binding fragment thereof of claim 1, wherein the antibody is directly or indirectly linked to an agent.

5. The BBB-selective antibody or antigen-binding fragment thereof of claim 4, wherein the agent is selected from the group consisting of a therapeutic agent, a pharmaceutical agent, a diagnostic agent, an imaging agent, a detection agent, an immunological therapeutic construct, and a combination thereof.

6. The BBB-selective antibody or antigen-binding fragment thereof of claim 5, wherein the agent is a therapeutic agent, a pharmaceutical agent, or a combination thereof.

7. The BBB-selective antibody or antigen-binding fragment of claim 5, wherein the agent is a diagnostic agent or an imaging agent.

8. The BBB-selective antibody or antigen-binding fragment thereof of claim 1, wherein the antibody is a scFv.

9. A blood brain barrier (BBB)-selective antibody or antigen-binding fragment thereof comprising a peptide encoded by a DNA sequence comprising (a) SEQ ID NO:16, SEQ ID NO: 17, SEQ ID NO: 18, SEQ ID NO: 19, SEQ ID NO:20 and SEQ ID NO:21, or (b) SEQ ID NO:23, SEQ ID NO:24, SEQ ID NO:25, SEQ ID NO:26, SEQ ID NO:27, and SEQ ID NO:28.

10. The BBB-selective antibody or antigen-binding fragment thereof of claim 9, wherein the DNA sequence comprises SEQ ID NO: 15 or SEQ ID NO:22.

11. The BBB-selective antibody or antigen-binding fragment thereof of claim 9, wherein the antibody is directly or indirectly linked to an agent.

12. The BBB-selective antibody or antigen-binding fragment thereof of claim 11, wherein the agent is selected from the group consisting of a therapeutic agent, a pharmaceutical agent, a diagnostic agent, an imaging agent, a detection agent-, a immunological therapeutic construct, and a combination thereof.

13. The BBB-selective antibody or antigen-binding fragment thereof of claim 12, wherein the agent is a therapeutic agent, a pharmaceutical agent, or a diagnostic agent.

14. The BBB-selective antibody or antigen-binding fragment thereof of claim 9, wherein the antibody is engrafted within a full IgG scaffold of human or other species or a scFv scaffold of human or other species.

15. The BBB-selective antibody or antigen-binding fragment thereof of claim 9, wherein the antibody is a humanized antibody or humanized antigen-binding fragment thereof.

16. A vector comprising a DNA encoding the BBB-selective antibody of claim 1.

17. A microorganism comprising the vector of claim 16.

18. A method of targeting an agent to the blood brain barrier of a subject comprising the steps of
   (a) administering to the subject a BBB-selective antibody or antigen-binding fragment thereof of claim 1, wherein the antibody is directly or indirectly linked to the agent, wherein the BBB-selective antibody or antigen-binding fragment thereof is able to specifically target the blood brain barrier.

19. The method of claim 18, wherein the agent is able to cross the blood brain barrier after targeting.

20. The method of claim 18, wherein the agent is delivered to the surface of the BBB after targeting.

21. A method of targeting a therapeutic agent to the blood brain barrier of a subject, the method comprising administering to the subject a BBB-selective antibody or antigen-binding fragment thereof of claim 1, wherein the antibody is directly or indirectly linked to the agent, wherein the BBB-selective antibody or antigen-binding fragment thereof is able to specifically target the blood brain barrier.

* * * * *

UNITED STATES PATENT AND TRADEMARK OFFICE
CERTIFICATE OF CORRECTION

| | | |
|---|---|---|
| PATENT NO. | : 12,161,889 B2 | Page 1 of 1 |
| APPLICATION NO. | : 17/260697 | |
| DATED | : December 10, 2024 | |
| INVENTOR(S) | : Eric V. Shusta et al. | |

It is certified that error appears in the above-identified patent and that said Letters Patent is hereby corrected as shown below:

In the Specification

Column 2, Line 33, "enrichment 18-20" should be --enrichment$^{18-20}$--.

Column 5, Line 38, "IgG. IgA." should be --IgG, IgA,--.

Column 7, Lines 13, "fungi: mammalian cells:" should be --fungi; mammalian cells;--.

Column 7, Line 15, "system:" should be --system;--.

Column 7, Line 17, "1:" should be --1;--.

Column 9, Line 21, "pairs." should be --pairs,--.

Column 10, Line 58, "scFV40)" should be --scFV40--.

Column 12, Line 21, "acid):" should be --acid);--.

Column 18, Line 44, "previously1$^4$" should be --previously$^{14}$--.

Column 22, Line 56, "5.9×106" should be --5.9×10$^6$- --.

Column 23, Line 1, "4-11-0.82" should be --4-11=0.82--.

Signed and Sealed this
Thirteenth Day of May, 2025

Coke Morgan Stewart
*Acting Director of the United States Patent and Trademark Office*

SEQUENCE LISTING

<160> NUMBER OF SEQ IDS: 41

<210> SEQ ID NO 1
<211> LENGTH: 244
<212> TYPE: PRT
<213> ORGANISM: Homo sapiens
<220> FEATURE:
<221> NAME/KEY: MISC_FEATURE
<222> LOCATION: (1)..(244)
<223> OTHER INFORMATION: scFv4

<400> SEQUENCE: 1

Gln Val Gln Leu Val Glu Ser Gly Gly Gly Leu Val Gln Pro Gly Gly

-continued

```
1               5                   10                  15
Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
                35                  40                  45

Ser Ala Ile Gly Gly Ser Gly Ser Thr Tyr Tyr Thr Glu Ser Val
                50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Ala Trp Asp Ser Tyr Ser Arg Lys Pro Asp Tyr Trp Gly Gln
                100                 105                 110

Gly Thr Leu Val Thr Val Ser Gly Gly Gly Ser Gly Gly Gly
                115                 120                 125

Gly Ser Gly Gly Gly Ser Asn Phe Met Leu Thr Gln Asp Pro Ala
                130                 135                 140

Val Ser Val Ala Leu Gly Gln Thr Val Arg Ile Thr Cys Gln Gly Asp
145                 150                 155                 160

Ser Leu Lys Ser His Tyr Ala Ser Trp Tyr His Gln Lys Pro Gly Gln
                165                 170                 175

Ala Pro Leu Leu Val Ile Tyr Asp Asn Asn Asn Arg Pro Ser Gly Val
                180                 185                 190

Pro Asp Arg Phe Ser Gly Ser Arg Ser Gly Thr Ser Ala Ser Leu Ala
                195                 200                 205

Ile Thr Gly Val Gln Ala Glu Asp Glu Ala Asp Tyr Tyr Cys Gln Ser
                210                 215                 220

Tyr Asp Ser Ser Leu Arg Gly Ser Arg Val Phe Gly Thr Gly Thr Lys
225                 230                 235                 240

Val Thr Val Leu

<210> SEQ ID NO 2
<211> LENGTH: 8
<212> TYPE: PRT
<213> ORGANISM: Homo sapiens
<220> FEATURE:
<221> NAME/KEY: MISC_FEATURE
<222> LOCATION: (1)..(8)
<223> OTHER INFORMATION: CDRH1 region of scFv4

<400> SEQUENCE: 2

Gly Phe Thr Phe Ser Ser Tyr Ala
1               5

<210> SEQ ID NO 3
<211> LENGTH: 8
<212> TYPE: PRT
<213> ORGANISM: Homo sapiens
<220> FEATURE:
<221> NAME/KEY: MISC_FEATURE
<222> LOCATION: (1)..(8)
<223> OTHER INFORMATION: CDRH2 region of scFv4

<400> SEQUENCE: 3

Ile Gly Gly Ser Gly Gly Ser Thr
1               5

<210> SEQ ID NO 4
<211> LENGTH: 11
```

```
<212> TYPE: PRT
<213> ORGANISM: Homo sapiens
<220> FEATURE:
<221> NAME/KEY: MISC_FEATURE
<222> LOCATION: (1)..(11)
<223> OTHER INFORMATION: CDRH3 region of scFv4

<400> SEQUENCE: 4

Ala Trp Asp Ser Tyr Ser Arg Lys Pro Asp Tyr
1               5                   10

<210> SEQ ID NO 5
<211> LENGTH: 6
<212> TYPE: PRT
<213> ORGANISM: Homo sapiens
<220> FEATURE:
<221> NAME/KEY: misc_feature
<222> LOCATION: (1)..(6)
<223> OTHER INFORMATION: CDRL1 region of scFv4

<400> SEQUENCE: 5

Ser Leu Lys Ser His Tyr
1               5

<210> SEQ ID NO 6
<211> LENGTH: 3
<212> TYPE: PRT
<213> ORGANISM: Homo sapiens
<220> FEATURE:
<221> NAME/KEY: MISC_FEATURE
<222> LOCATION: (1)..(3)
<223> OTHER INFORMATION: CDRL2 region of scFv4

<400> SEQUENCE: 6

Asp Asn Asn
1

<210> SEQ ID NO 7
<211> LENGTH: 12
<212> TYPE: PRT
<213> ORGANISM: Homo sapiens
<220> FEATURE:
<221> NAME/KEY: MISC_FEATURE
<222> LOCATION: (1)..(12)
<223> OTHER INFORMATION: CDRL3 region of scFv4

<400> SEQUENCE: 7

Gln Ser Tyr Asp Ser Ser Leu Arg Gly Ser Arg Val
1               5                   10

<210> SEQ ID NO 8
<211> LENGTH: 248
<212> TYPE: PRT
<213> ORGANISM: Homo sapiens
<220> FEATURE:
<221> NAME/KEY: misc_feature
<222> LOCATION: (1)..(248)
<223> OTHER INFORMATION: svFv40

<400> SEQUENCE: 8

Gln Val Gln Leu Gln Glu Ser Gly Gly Gly Leu Val Gln Ala Gly Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Leu Ala Pro Gly Lys Gly Leu Glu Trp Val
        35                  40                  45

Ser Ala Ile Ser Gly Ser Gly Arg Ser Thr Asn Tyr Ala Asp Ser Val
```

```
                50             55             60
Lys Gly Arg Phe Thr Ile Phe Arg Asp Asn Ser Lys Asn Thr Leu Tyr
 65              70              75              80

Leu Gln Met Asn Ser Leu Arg Ala Glu Asp Thr Ala Val Tyr Tyr Cys
                 85              90              95

Ala Lys Leu His Ser Glu Asp Ser Ser Gly Trp Arg Val Phe Asp Ile
                100             105             110

Trp Gly Gln Gly Thr Met Val Thr Val Ser Ser Gly Gly Gly Gly Ser
                115             120             125

Gly Gly Gly Gly Ser Gly Gly Arg Ser Gln Pro Glu Leu Thr Gln
                130             135             140

Asp Pro Ala Val Ser Gly Ser Pro Gly Gln Ser Ile Thr Ile Ser Tyr
145             150             155             160

Thr Gly Thr Ser Ser Asp Val Gly Gly Tyr Asn Tyr Val Ser Trp Tyr
                165             170             175

Gln Gln His Pro Gly Lys Ala Pro Lys Leu Met Ile Tyr Glu Val Ser
                180             185             190

Asn Arg Pro Ser Gly Val Ser Asn Arg Phe Ser Gly Ser Lys Ser Gly
                195             200             205

Asn Thr Ala Ser Leu Thr Ile Ser Gly Leu Gln Ala Glu Asp Glu Ala
                210             215             220

Asp Tyr Tyr Cys Ser Ser Tyr Thr Asp Ser Asn Val Val Phe Gly Gly
225             230             235             240

Gly Thr Lys Leu Thr Val Leu Gly
                245

<210> SEQ ID NO 9
<211> LENGTH: 8
<212> TYPE: PRT
<213> ORGANISM: Homo sapiens
<220> FEATURE:
<221> NAME/KEY: MISC_FEATURE
<222> LOCATION: (1)..(8)
<223> OTHER INFORMATION: CDRH1 region of svFv40

<400> SEQUENCE: 9

Gly Phe Thr Phe Ser Ser Tyr Gly
1               5

<210> SEQ ID NO 10
<211> LENGTH: 8
<212> TYPE: PRT
<213> ORGANISM: Homo sapiens
<220> FEATURE:
<221> NAME/KEY: MISC_FEATURE
<222> LOCATION: (1)..(8)
<223> OTHER INFORMATION: CDRH2 region of svFv40

<400> SEQUENCE: 10

Ile Ser Gly Ser Gly Arg Ser Thr
1               5

<210> SEQ ID NO 11
<211> LENGTH: 13
<212> TYPE: PRT
<213> ORGANISM: Homo sapiens
<220> FEATURE:
<221> NAME/KEY: MISC_FEATURE
<222> LOCATION: (1)..(13)
<223> OTHER INFORMATION: CDRH3 region of svFv40

<400> SEQUENCE: 11
```

Leu His Ser Glu Asp Ser Ser Gly Trp Arg Val Phe Asp
1               5                   10

<210> SEQ ID NO 12
<211> LENGTH: 9
<212> TYPE: PRT
<213> ORGANISM: Homo sapiens
<220> FEATURE:
<221> NAME/KEY: MISC_FEATURE
<222> LOCATION: (1)..(9)
<223> OTHER INFORMATION: CDRL1 region of svFv40

<400> SEQUENCE: 12

Ser Ser Asp Val Gly Gly Tyr Asn Tyr
1               5

<210> SEQ ID NO 13
<211> LENGTH: 3
<212> TYPE: PRT
<213> ORGANISM: Homo sapiens
<220> FEATURE:
<221> NAME/KEY: MISC_FEATURE
<222> LOCATION: (1)..(3)
<223> OTHER INFORMATION: CDRL2 region of svFv40

<400> SEQUENCE: 13

Glu Val Ser
1

<210> SEQ ID NO 14
<211> LENGTH: 9
<212> TYPE: PRT
<213> ORGANISM: Homo sapiens
<220> FEATURE:
<221> NAME/KEY: MISC_FEATURE
<222> LOCATION: (1)..(9)
<223> OTHER INFORMATION: CDRL3 region of svFv40

<400> SEQUENCE: 14

Ser Ser Tyr Thr Asp Ser Asn Val Val
1               5

<210> SEQ ID NO 15
<211> LENGTH: 734
<212> TYPE: DNA
<213> ORGANISM: Homo sapiens
<220> FEATURE:
<221> NAME/KEY: misc_feature
<222> LOCATION: (1)..(734)
<223> OTHER INFORMATION: scFv4

<400> SEQUENCE: 15
caggtgcagc tggtggagtc tgggggaggc ttggtacagc ctgggggtc cctgagactc      60 tcctgtgcag cctctggatt cacctttagc agctatgcca tgagctgggt ccgccaggct    120
ccagggaagg gctggagtg gtctcagct attggtggta gtggtggtag cacatactac     180
acagagtccg tgaagggccg gttcaccatc tccagagaca attccaagaa cacgctgtat    240
ctgcaaatga acagcctgag agccgaggac acggccgtat attactgtgc gaaagcctgg    300
gattcgtata gtaggaaacc tgactactgg ggccagggca ccctggtcac cgtctcctca    360
ggtggaggcg gttcaggcgg aggtggctct ggcggtggcg gatcgaattt tatgctgact    420 caggacccctg ctgtgtctgt ggccttggga cagacagtca ggatcacatg ccaaggagac    480
agcctcaaaa gccattatgc aagctggtac catcagaagc caggacaggc ccctctactt    540

```
gtcatctatg ataacaacaa tcggccctca ggggtccctg accgattctc tggctccagg    600
tctggcacct cagcctccct ggccatcact ggggtccagg ctgaagatga ggctgactat    660
tactgccagt catatgacag cagcctgagg ggttcgaggg tcttcggaac tgggaccaag    720
gtcaccgtcc tagt                                                      734
```

```
<210> SEQ ID NO 16
<211> LENGTH: 24
<212> TYPE: DNA
<213> ORGANISM: Homo sapiens
<220> FEATURE:
<221> NAME/KEY: misc_feature
<222> LOCATION: (1)..(24)
<223> OTHER INFORMATION: CDRH1 region of scFv4

<400> SEQUENCE: 16
ggattcacct ttagcagcta tgcc                                           24

<210> SEQ ID NO 17
<211> LENGTH: 24
<212> TYPE: DNA
<213> ORGANISM: Homo sapiens
<220> FEATURE:
<221> NAME/KEY: misc_feature
<222> LOCATION: (1)..(24)
<223> OTHER INFORMATION: CDRH2 region of scFv4

<400> SEQUENCE: 17
attggtggta gtggtggtag caca                                           24

<210> SEQ ID NO 18
<211> LENGTH: 39
<212> TYPE: DNA
<213> ORGANISM: Homo sapiens
<220> FEATURE:
<221> NAME/KEY: misc_feature
<222> LOCATION: (1)..(39)
<223> OTHER INFORMATION: CDRH3 region of scFv4

<400> SEQUENCE: 18
gcgaaagcct gggattcgta tagtaggaaa cctgactac                           39

<210> SEQ ID NO 19
<211> LENGTH: 18
<212> TYPE: DNA
<213> ORGANISM: Homo sapiens
<220> FEATURE:
<221> NAME/KEY: misc_feature
<222> LOCATION: (1)..(18)
<223> OTHER INFORMATION: CDRL1 region of scFv4

<400> SEQUENCE: 19
agcctcaaaa gccattat                                                  18

<210> SEQ ID NO 20
<211> LENGTH: 9
<212> TYPE: DNA
<213> ORGANISM: Homo sapiens
<220> FEATURE:
<221> NAME/KEY: misc_feature
<222> LOCATION: (1)..(9)
<223> OTHER INFORMATION: CDRL2 region of scFv4

<400> SEQUENCE: 20 gataacaac                                                             9
```

<210> SEQ ID NO 21
<211> LENGTH: 36
<212> TYPE: DNA
<213> ORGANISM: Homo sapiens
<220> FEATURE:
<221> NAME/KEY: misc_feature
<222> LOCATION: (1)..(36)
<223> OTHER INFORMATION: CDRL3 region of scFv4

<400> SEQUENCE: 21
cagtcatatg acagcagcct gaggggttcg agggtc                                36

<210> SEQ ID NO 22
<211> LENGTH: 744
<212> TYPE: DNA
<213> ORGANISM: Homo sapiens
<220> FEATURE:
<221> NAME/KEY: misc_feature
<222> LOCATION: (1)..(744)
<223> OTHER INFORMATION: scFv40

<400> SEQUENCE: 22
caggtgcagc tgcaggagtc ggggggaggc ttggtacagg cggggggtc cctcagactc        60 tcctgtgcag cctctggatt cacctttagc agctatggca tgagctgggt ccgcctggct      120
ccggggaagg ggctggagtg ggtctcagct attagtggta gtggacgtag cacaaactac      180
gcagactccg tgaagggccg gttcaccatc tcagagaca attccaagaa cacgctgtat       240
ctgcaaatga acagcctgag agccgaggac acggccgtat attactgtgc gaaactccat     300
agtgaggata gcagtggctg gagagttttt gatatctggg gccaagggac aatggtcacc     360
gtctcttcag gtggaggcgg ttcaggcgga ggtggctctg gcggtggcag atcgcagcct    420
gagctgactc aggaccctgc tgtgtctggg tctcctggac agtcgatcac catctcctac    480
actggaacca gcagtgacgt tggtggttat aactatgtct cctggtacca acagcaccca   540
ggcaaagccc ccaaactcat gatttatgag gtcagtaatc ggccctcagg gtttctaat    600 cgcttctctg gctccaagtc tggcaacacg gcctccctga ccatctctgg gctccaggct    660
gaggacgagg ctgattatta ctgcagctca tatacagaca gcaatgtggt attcggcgga   720
gggaccaagc tgaccgtcct aggt                                          744

<210> SEQ ID NO 23
<211> LENGTH: 24
<212> TYPE: DNA
<213> ORGANISM: Homo sapiens
<220> FEATURE:
<221> NAME/KEY: misc_feature
<222> LOCATION: (1)..(24)
<223> OTHER INFORMATION: CDRH1 region of svFv40

<400> SEQUENCE: 23
ggattcacct ttagcagcta tggc                                            24

<210> SEQ ID NO 24
<211> LENGTH: 24
<212> TYPE: DNA
<213> ORGANISM: Homo sapiens
<220> FEATURE:
<221> NAME/KEY: misc_feature
<222> LOCATION: (1)..(24)
<223> OTHER INFORMATION: CDRH2 region of svFv40

<400> SEQUENCE: 24
attagtggta gtggacgtag caca                                            24

```
<210> SEQ ID NO 25
<211> LENGTH: 45
<212> TYPE: DNA
<213> ORGANISM: Homo sapiens
<220> FEATURE:
<221> NAME/KEY: misc_feature
<222> LOCATION: (1)..(45)
<223> OTHER INFORMATION: CDRH3 region of svFv40

<400> SEQUENCE: 25
gcgaaactcc atagtgagga tagcagtggc tggagagttt ttgat           45

<210> SEQ ID NO 26
<211> LENGTH: 27
<212> TYPE: DNA
<213> ORGANISM: Homo sapiens
<220> FEATURE:
<221> NAME/KEY: misc_feature
<222> LOCATION: (1)..(27)
<223> OTHER INFORMATION: CDRL1 region of svFv40

<400> SEQUENCE: 26
agcagtgacg ttggtggtta taactat                               27

<210> SEQ ID NO 27
<211> LENGTH: 9
<212> TYPE: DNA
<213> ORGANISM: Homo sapiens
<220> FEATURE:
<221> NAME/KEY: misc_feature
<222> LOCATION: (1)..(9)
<223> OTHER INFORMATION: CDRL2 region of svFv40

<400> SEQUENCE: 27 gaggtcagt                                                    9

<210> SEQ ID NO 28
<211> LENGTH: 27
<212> TYPE: DNA
<213> ORGANISM: Homo sapiens
<220> FEATURE:
<221> NAME/KEY: misc_feature
<222> LOCATION: (1)..(27)
<223> OTHER INFORMATION: CDRL3 region of svFv40

<400> SEQUENCE: 28
agctcatata cagacagcaa tgtggta                               27

<210> SEQ ID NO 29
<211> LENGTH: 19
<212> TYPE: DNA
<213> ORGANISM: Artificial Sequence
<220> FEATURE:
<223> OTHER INFORMATION: Reverse primer for the amplification of human
      CDR-H3's

<400> SEQUENCE: 29
gaaccgcctc cacctgagg                                        19

<210> SEQ ID NO 30
<211> LENGTH: 27
<212> TYPE: DNA
<213> ORGANISM: Artificial Sequence
<220> FEATURE:
<223> OTHER INFORMATION: Reverse primer for the amplification of scFv

<400> SEQUENCE: 30
```

```
gaattttctg tatgaggttt tgctaaa                                        27
```

<210> SEQ ID NO 31
<211> LENGTH: 22
<212> TYPE: DNA
<213> ORGANISM: Artificial Sequence
<220> FEATURE:
<223> OTHER INFORMATION: Foward primer for the amplification of scFv
<220> FEATURE:
<221> NAME/KEY: misc_feature
<222> LOCATION: (1)..(22)
<223> OTHER INFORMATION: Forward primer for amplification of scFv

<400> SEQUENCE: 31

```
tttttggaga ttttcaacgt ga                                             22
```

<210> SEQ ID NO 32
<211> LENGTH: 13
<212> TYPE: PRT
<213> ORGANISM: Homo sapiens
<220> FEATURE:
<221> NAME/KEY: misc_feature
<222> LOCATION: (1)..(13)
<223> OTHER INFORMATION: CDR-H3 region of scFv clone 1

<400> SEQUENCE: 32

Gly Ala Leu Gln Ser Gly Ser Tyr Tyr Pro Pro Gly Tyr
1               5                   10

<210> SEQ ID NO 33
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR-H3 region of scFv clone 2

<400> SEQUENCE: 33

Asp Asn Gly Glu Tyr
1               5

<210> SEQ ID NO 34
<211> LENGTH: 8
<212> TYPE: PRT
<213> ORGANISM: Homo sapiens
<220> FEATURE:
<221> NAME/KEY: MISC_FEATURE
<222> LOCATION: (1)..(8)
<223> OTHER INFORMATION: CDR-H3 region of scFv clone 6

<400> SEQUENCE: 34

Ala Asp Gly Gly Asn Ser Asp Tyr
1               5

<210> SEQ ID NO 35
<211> LENGTH: 13
<212> TYPE: PRT
<213> ORGANISM: Homo sapiens
<220> FEATURE:
<221> NAME/KEY: MISC_FEATURE
<222> LOCATION: (1)..(13)
<223> OTHER INFORMATION: CDR-H3 region of scFv clone 8

<400> SEQUENCE: 35

Gly Ser Met Val Arg Gly Pro Tyr Pro Arg Phe Asp Pro
1               5                   10

-continued

```
<210> SEQ ID NO 36
<211> LENGTH: 12
<212> TYPE: PRT
<213> ORGANISM: Homo sapiens
<220> FEATURE:
<221> NAME/KEY: MISC_FEATURE
<222> LOCATION: (1)..(12)
<223> OTHER INFORMATION: CDR-H3 region of scFv clone 10

<400> SEQUENCE: 36

Glu Thr Gly Ala Tyr Tyr Tyr Tyr Gly Met Asp Val
1               5                   10

<210> SEQ ID NO 37
<211> LENGTH: 13
<212> TYPE: PRT
<213> ORGANISM: Homo sapiens
<220> FEATURE:
<221> NAME/KEY: MISC_FEATURE
<222> LOCATION: (1)..(13)
<223> OTHER INFORMATION: CDR-H3 region of scFv clone 11

<400> SEQUENCE: 37

Asp Arg Trp Leu Gln Asn Trp Glu Arg Pro Phe Asp Tyr
1               5                   10

<210> SEQ ID NO 38
<211> LENGTH: 12
<212> TYPE: PRT
<213> ORGANISM: Homo sapiens
<220> FEATURE:
<221> NAME/KEY: MISC_FEATURE
<222> LOCATION: (1)..(12)
<223> OTHER INFORMATION: CDR-H3 region of scFv clone 17

<400> SEQUENCE: 38

Tyr Tyr Tyr Asp Ser Ser Ala Phe Met Thr Gly Asn
1               5                   10

<210> SEQ ID NO 39
<211> LENGTH: 16
<212> TYPE: PRT
<213> ORGANISM: Homo sapiens
<220> FEATURE:
<221> NAME/KEY: MISC_FEATURE
<222> LOCATION: (1)..(16)
<223> OTHER INFORMATION: CDR-H3 region of scFv clone 18

<400> SEQUENCE: 39

Asp Leu Tyr Asp Ser Ser Gly Asn Leu His Gly Asn Trp Phe Asp Pro
1               5                   10                  15

<210> SEQ ID NO 40
<211> LENGTH: 21
<212> TYPE: PRT
<213> ORGANISM: Homo sapiens
<220> FEATURE:
<221> NAME/KEY: MISC_FEATURE
<222> LOCATION: (1)..(21)
<223> OTHER INFORMATION: CDR-H3 region of scFv clone 23

<400> SEQUENCE: 40

Asp Leu His Leu Ser Ile Ala Ala Ala Gly Thr Gly Val Phe Lys Thr
1               5                   10                  15

Pro Leu Arg Asp Tyr
            20

<210> SEQ ID NO 41
```

```
<211> LENGTH: 10
<212> TYPE: PRT
<213> ORGANISM: Homo sapiens
<220> FEATURE:
<221> NAME/KEY: MISC_FEATURE
<222> LOCATION: (1)..(10)
<223> OTHER INFORMATION: CDR-H3 region of scFv clone 59

<400> SEQUENCE: 41

Arg Leu Gly Tyr Ser Ala Pro Gly Asp Tyr
1               5                   10
```